United States Patent [19]
Avruch et al.

[11] Patent Number: 5,736,337
[45] Date of Patent: Apr. 7, 1998

[54] INHIBITING PROTEIN INTERACTIONS

[75] Inventors: Joseph Avruch, Brookline; Xian-feng Zhang, Cambridge, both of Mass.; Mark S. Marshall, Carmel, Ind.

[73] Assignees: The General Hospital Corporation, Boston, Mass.; Indiana University Foundation, Bloomington, Ind.

[21] Appl. No.: 259,672

[22] Filed: Jun. 10, 1994

Related U.S. Application Data

[63] Continuation-in-part of Ser. No. 77,256, Jun. 11, 1993, Pat. No. 5,582,995.

[51] Int. Cl.$^6$ ............................................. G01N 33/53
[52] U.S. Cl. .................... 435/7.1; 435/7.21; 435/7.23; 435/172.1; 436/501; 436/518; 436/536; 436/63; 436/64
[58] Field of Search ........................ 435/7.1, 7.21, 435/7.23, 172.1; 436/501, 518, 536, 63, 64

[56] References Cited

PUBLICATIONS

Dermer, Bio/Technology, vol. 12 Mar. 1994, p.320 "Another for the War on Cancer".
Beardsley, T., "Design for Living: A Signaling Pathway Found in Many Species is Mapped", 1994 Scientific American, pp. 28 and 32.
Chung, D.L., et al., "A Peptide from the Gap–Binding Domain of the ras–p21 Protein as well as Azatyrosine Block ras–induced Maturation of Xenopus Oocytes", 1991, Biochem. and Biophys. Research Commun., 181(3):1378–84.
Chung, D.L. et al., "A Peptide for the GAP–Binding Domain of the ras–p21 Protein and Azatyrosine Block ras–Induced Maturation of Xenopus Oocytes", 1991, Anticancer Research, 11:1373–78.
Cook, S.J., et al., "Inhibition by cAMP of Ras–Dependent Activation of Raf", 1993, Science 262:1069–72.
Crews, C.M., et al., "Extracellular Signals and Reversible Protein Phosphorylation: What to Mek of It All", 1993, Cell: Minireview, 74(2), pp. 215–217.
Feig, L.A., "The Many Roads That Lead to Ras", 1993, Science, 260:767–68.
Hall, A., "A Biochemical Function for Ras–At Last", 1994, Science, 264:1413–14.

Koide, H., et al., "GTP–dependent Association of Raf–1 with Ha–Ras: Identification of Raf as a Target Downstream of Ras in Mammalian Cells", 1993, Proc. Natl. Acad. Sci. USA, 90(18):8683–86.
Leevers, S.J., et al., "Requirement for Ras in Raf Activation is Overcome by Targeting Raf to the Plasma Membrane", 1994, Nature, 369:411–14.
Luban, J., et al., "Genetic Assay for Multimerization of Retroviral gag Polyproteins", 1992, J. Virology, 66(8):5157–60.
Moodie, S.A., et al., "Complexes of Ras–GTP with Raf–1 and Mitogen–Activated Protein Kinase Kinase", 1993, Science, 260:1658–61.
Mulcahy, L.S., et al., "Requirement for ras proto–oncogene function during serum–stimulated growth of NIH 3T3 Cells", 1985, Nature, 313:241–43.
Perrimon, N., et al., "The Torso Receptor Protein–Tyrosine Kinase Signaling Pathway: An Endless Story", 1993, Cell, 74(2):219–22.
Schaber, M.D., et al., "Ras Interaction with the GTPase–Activating Protein (GAP)", 1989, Proteins: Structure, Function, and Genetics, 6:306–15.
Scolnick, E.M., "The Partnership of Academia and Industry in Pharmacologic Research", 1991, J. Lab. Clin. Med., 117(1):8–14.
Van Aelst, L., et al., "Complex Formation Between RAS and RAF and Other Protein Kinases", 1993, Proc. Natl. Acad. Sci. USA, 90:6213–17.
Vojtek, A.B., et al., "Mammalian Ras Interacts Directly with the Serine/Threonine Kinase Raf", 1993, Cell, 74(1):205–14.
Warne, P.H., et al., "Direct Interaction of Ras and the Amino–Terminal Region of Raf–1 in Vitro", 1993, Nature, 364:352–55.
Wu, J., et al., "Inhibition of the EGF–Activated MAP Kinase Signaling Pathway by Adenosine 3',5'–Monophosphate", 1993, Science, 262:1065–69.
Zhang, X., et al., "Normal and Oncogenci p21$^{ras}$ Proteins Bind to the Amino–Terminal Regulatory Domain of c–Raf–1", 1993, Nature, 364:308–13.

*Primary Examiner*—Lora M. Green
*Attorney, Agent, or Firm*—Fish & Richardson P.C.

[57] ABSTRACT

Disclosed is a method of evaluating an anti-proliferative compound by contacting the compound with a Raf and determining its ability to bind to Ras, and methods of inhibiting cell proliferation in an animal by administering a compound which reduces the interaction of Ras with Raf.

18 Claims, 11 Drawing Sheets

| Peptide | | % Inhibition | |
|---|---|---|---|
| | ·  *   *    · · ·          *    * | | |
| Ras 17–31 | SALTIQLIQNHFVDEYDPTIEDSYRKQVVIDGETC | | (SEQ ID NO: 13) |
| Ras 22–36 | SALTIQLIQNHFVDE | 28 ± 6 | (SEQ ID NO: 14) |
| Ras 27–41 | QLIQNHFVDEYDPTI | 48 ± 6 | (SEQ ID NO: 15) |
| Ras 32–46 | HFVDEYDPTIEDSYR | 51 ± 8 | (SEQ ID NO: 16) |
| Ras 37–51 | YDPTIEDSYRKQVVI | 50 ± 13 | (SEQ ID NO: 17) |
| | EDSYRKQVVIDGETC | 75 ± 11 | (SEQ ID NO: 12) |
| Raf 51–65 | PSKTSNTIRVFLPNK | 0 ± 0 | (SEQ ID NO: 18) |

· indicates typical effector residues.
* indicates activator residues.

FIG. 11

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
    ( A ) LENGTH: 257
    ( B ) TYPE: amino acid
    ( C ) STRANDEDNESS:
    ( D ) TOPOLOGY: linear ( x i ) SEQUENCE DESCRIPTION: SEQ ID NO: 1:

```
Met Glu His Ile Gln Gly Ala Trp Lys Thr Ile Ser Asn Gly Phe Gly
  1               5                  10                  15

Phe Lys Asp Ala Val Phe Asp Gly Ser Ser Cys Ile Ser Pro Thr Ile
                 20                  25                  30

Val Gln Gln Phe Gly Tyr Gln Arg Arg Ala Ser Asp Asp Gly Lys Leu
             35                  40                  45

Thr Asp Pro Ser Lys Thr Ser Asn Thr Ile Arg Val Phe Leu Pro Asn
         50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
```

```
                    115                         120                         125
Asp Phe Leu Asp His Val Pro Leu Thr Thr His Asn Phe Ala Arg Lys
        130                     135                 140
Thr Phe Leu Lys Leu Ala Phe Cys Asp Ile Cys Gln Lys Phe Leu Leu
145                     150                     155                         160
Asn Gly Phe Arg Cys Gln Thr Cys Gly Tyr Lys Phe His Glu His Cys
                165                     170                     175
    Ser Thr Lys Val Pro Thr Met Cys Val Asp Trp Ser Asn Ile Arg Gln
                180                     185                     190
Leu Leu Leu Phe Pro Asn Ser Thr Ile Gly Asp Ser Gly Val Pro Ala
            195                     200                 205
Leu Pro Ser Leu Thr Met Arg Arg Met Arg Glu Ser Val Ser Arg Met
        210                     215                 220
Pro Val Ser Ser Gln His Arg Tyr Ser Thr Pro His Ala Phe Thr Phe
225                     230                     235                         240
Asn Thr Ser Ser Pro Ser Ser Glu Gly Ser Leu Ser Gln Arg Gln Arg
                245                     250                     255
Ser
```

( 2 ) INFORMATION FOR SEQ ID NO: 2:

( i ) SEQUENCE CHARACTERISTICS:
        ( A ) LENGTH: 17
        ( B ) TYPE: amino acid
        ( C ) STRANDEDNESS:
        ( D ) TOPOLOGY: linear ( x i ) SEQUENCE DESCRIPTION: SEQ ID NO: 2:

```
Cys Asp Ile Cys Gln Lys Phe Leu Leu Asn Gly Phe Arg Cys Gln Thr
1               5                       10                      15
Cys
```

( 2 ) INFORMATION FOR SEQ ID NO: 3:

( i ) SEQUENCE CHARACTERISTICS:
        ( A ) LENGTH: 186
        ( B ) TYPE: amino acid
        ( C ) STRANDEDNESS:
        ( D ) TOPOLOGY: linear ( x i ) SEQUENCE DESCRIPTION: SEQ ID NO: 3:

```
Met Thr Glu Tyr Lys Leu Val Val Val Gly Ala Gly Gly Val Gly Lys
1               5                       10                      15
Ser Ala Leu Thr Ile Gln Leu Ile Gln Asn His Phe Val Asp Glu Tyr
            20                      25                  30
Asp Pro Thr Ile Glu Asp Ser Tyr Arg Lys Gln Val Val Ile Asp Gly
        35                      40                      45
Glu Thr Cys Leu Leu Asp Ile Leu Asp Thr Ala Gly Gln Glu Glu tyr
    50                      55                      60
Ser Ala Met Arg Asp Gln Tyr Met Arg Thr Gly Glu Gly Phe Leu Cys
65                      70                      75                          80
Val Phe Ala Ile Asn Asn Thr Lys Ser Phe Glu Asp Ile His Gln Tyr
                85                      90                      95
Arg Glu Gln Ile Lys Arg Val Lys Asp Ser Asp Asp Val Pro Met Val
                100                     105                     110
Leu Val Gly Asn Lys Cys Asp Leu Ala Ala Arg Thr Val Glu Ser Arg
            115                     120                     125
Gln Ala Gln Asp Leu Ala Arg Ser Tyr Gly Ile Pro Tyr Ile Glu Thr
```

```
                    130                      135                         140
Ser  Ala  Lys  Thr  Arg  Gln  Gly  Val  Glu  Asp  Ala  Phe  Tyr  Thr  Leu  Val
145                      150                      155                         160

Arg  Glu  Ile  Arg  Gln  His  Lys  Leu  Arg  Lys  Leu  Asn  Pro  Pro  Asp  Glu
                         165                      170                    175

Ser  Gly  Pro  Gly  Cys  Met  Ser  Cys  Lys  Cys
                    180                      185
```

( 2 ) INFORMATION FOR SEQ ID NO: 4:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 4:

```
Tyr  Asp  Pro  Thr  Ile  Glu  Asp  Ser  Tyr
1                        5
```

( 2 ) INFORMATION FOR SEQ ID NO: 5:

( i ) SEQUENCE CHARACTERISTICS:
        ( A ) LENGTH: 17
        ( B ) TYPE: amino acid
        ( C ) STRANDEDNESS:
        ( D ) TOPOLOGY: linear ( x i ) SEQUENCE DESCRIPTION: SEQ ID NO: 5:

```
Cys  Xaa  Xaa  Cys  Xaa  Xaa  Xaa  Xaa  Xaa  Xaa  Xaa  Xaa  Cys  Xaa  Xaa
1                        5                        10                   15

Cys
```

( 2 ) INFORMATION FOR SEQ ID NO: 6:

( i ) SEQUENCE CHARACTERISTICS:
        ( A ) LENGTH: 149
        ( B ) TYPE: amino acid
        ( C ) STRANDEDNESS:
        ( D ) TOPOLOGY: linear ( x i ) SEQUENCE DESCRIPTION: SEQ ID NO: 6:

```
Met  Glu  His  Ile  Gln  Gly  Ala  Trp  Lys  Thr  Ile  Ser  Asn  Gly  Phe  Gly
                    5                        10                       15

Phe  Lys  Asp  Ala  Val  Phe  Asp  Gly  Ser  Ser  Cys  Ile  Ser  Pro  Thr  Ile
               20                       25                       30

Val  Gln  Gln  Phe  Gly  Tyr  Gln  Arg  Arg  Ala  Ser  Asp  Asp  Gly  Lys  Leu
          35                       40                       45

Thr  Asp  Pro  Ser  Lys  Thr  Ser  Asn  Thr  Ile  Arg  Val  Phe  Leu  Pro  Asn
     50                       55                       60

Lys  Gln  Arg  Thr  Val  Val  Asn  Val  Arg  Asn  Gly  Met  Ser  Leu  His  Asp
65                       70                       75                        80

Cys  Leu  Met  Lys  Ala  Leu  Lys  Val  Arg  Gly  Leu  Gln  Pro  Glu  Cys  Cys
                    85                       90                       95

Ala  Val  Phe  Arg  Leu  Leu  His  Glu  His  Lys  Gly  Lys  Lys  Ala  Arg  Leu
               100                      105                      110

Asp  Trp  Asn  Thr  Asp  Ala  Ala  Ser  Leu  Ile  Gly  Glu  Glu  Leu  Gln  Val
          115                      120                      125

Asp  Phe  Leu  Asp  His  Val  Pro  Leu  Thr  Thr  His  Asn  Phe  Ala  Arg  Lys
     130                      135                      140

Thr  Phe  Leu  Lys  Leu
```

( 2 ) INFORMATION FOR SEQ ID NO: 7:

( i ) SEQUENCE CHARACTERISTICS:
        ( A ) LENGTH: 99
        ( B ) TYPE: amino acid
        ( C ) STRANDEDNESS:
        ( D ) TOPOLOGY: linear ( x i ) SEQUENCE DESCRIPTION: SEQ ID NO: 7:

```
Pro  Ser  Lys  Thr  Ser  Asn  Thr  Ile  Arg  Val  Phe  Leu  Pro  Asn  Lys  Gln
               5                        10                       15
Arg  Thr  Val  Val  Asn  Val  Arg  Asn  Gly  Met  Ser  Leu  His  Asp  Cys  Leu
          20                       25                       30
Met  Lys  Ala  Leu  Lys  Val  Arg  Gly  Leu  Gln  Pro  Glu  Cys  Cys  Ala  Val
     35                       40                       45
Phe  Arg  Leu  Leu  His  Glu  His  Lys  Gly  Lys  Lys  Ala  Arg  Leu  Asp  Trp
     50                  55                       60
Asn  Thr  Asp  Ala  Ala  Ser  Leu  Ile  Gly  Glu  Glu  Leu  Gln  Val  Asp  Phe
65                       70                  75                            80
Leu  Asp  His  Val  Pro  Leu  Thr  Thr  His  Asn  Phe  Ala  Arg  Lys  Thr  Phe
               85                       90                       95
Leu  Lys  Leu
```

( 2 ) INFORMATION FOR SEQ ID NO: 8:

( i ) SEQUENCE CHARACTERISTICS:
        ( A ) LENGTH: 81
        ( B ) TYPE: amino acid
        ( C ) STRANDEDNESS:
        ( D ) TOPOLOGY: linear ( x i ) SEQUENCE DESCRIPTION: SEQ ID NO: 8:

```
Pro  Ser  Lys  Thr  Ser  Asn  Thr  Ile  Arg  Val  Phe  Leu  Pro  Asn  Lys  Gln
               5                        10                       15
Arg  Thr  Val  Val  Asn  Val  Arg  Asn  Gly  Met  Ser  Leu  His  Asp  Cys  Leu
          20                       25                       30
Met  Lys  Ala  Leu  Lys  Val  Arg  Gly  Leu  Gln  Pro  Glu  Cys  Cys  Ala  Val
     35                       40                       45
Phe  Arg  Leu  Leu  His  Glu  His  Lys  Gly  Lys  Lys  Ala  Arg  Leu  Asp  Trp
     50                  55                       60
Asn  Thr  Asp  Ala  Ala  Ser  Leu  Ile  Gly  Glu  Glu  Leu  Gln  Val  Asp  Phe
65                       70                  75                            80
Leu
```

( 2 ) INFORMATION FOR SEQ ID NO: 9:

( i ) SEQUENCE CHARACTERISTICS:
        ( A ) LENGTH: 32
        ( B ) TYPE: amino acid
        ( C ) STRANDEDNESS:
        ( D ) TOPOLOGY: linear ( x i ) SEQUENCE DESCRIPTION: SEQ ID NO: 9:

```
Leu  Asp  Trp  Asn  Thr  Asp  Ala  Ala  Ser  Leu  Ile  Gly  Glu  Glu  Leu  Gln
               5                        10                       15
Val  Asp  Phe  Leu  Asp  His  Val  Pro  Leu  Thr  Thr  His  Asn  Phe  Ala  Arg
          20                       25                       30
```

( 2 ) INFORMATION FOR SEQ ID NO: 10:

( i ) SEQUENCE CHARACTERISTICS:
   ( A ) LENGTH: 18
   ( B ) TYPE: amino acid
   ( C ) STRANDEDNESS:
   ( D ) TOPOLOGY: linear ( x i ) SEQUENCE DESCRIPTION: SEQ ID NO: 10:

Val Arg Gly Leu Gln Pro Glu Cys Cys Ala Val Phe Arg Leu Leu His
                  5                   10                  15
Glu His ( 2 ) INFORMATION FOR SEQ ID NO: 11:

( i ) SEQUENCE CHARACTERISTICS:
      ( A ) LENGTH: 15
      ( B ) TYPE: amino acid
      ( C ) STRANDEDNESS:
      ( D ) TOPOLOGY: linear ( x i ) SEQUENCE DESCRIPTION: SEQ ID NO: 11:

Leu Gln Pro Glu Cys Cys Ala Val Phe Arg Leu Leu His Glu His
                5                   10                  15

( 2 ) INFORMATION FOR SEQ ID NO: 12:

( i ) SEQUENCE CHARACTERISTICS:
      ( A ) LENGTH: 15
      ( B ) TYPE: amino acid
      ( C ) STRANDEDNESS:
      ( D ) TOPOLOGY: linear ( x i ) SEQUENCE DESCRIPTION: SEQ ID NO: 12:

Glu Asp Ser Tyr Arg Lys Gln Val Val Ile Asp Gly Glu Thr Cys
                5                   10                  15

( 2 ) INFORMATION FOR SEQ ID NO: 13:

( i ) SEQUENCE CHARACTERISTICS:
      ( A ) LENGTH: 35
      ( B ) TYPE: amino acid
      ( C ) STRANDEDNESS:
      ( D ) TOPOLOGY: linear ( x i ) SEQUENCE DESCRIPTION: SEQ ID NO: 13:

Ser Ala Leu Thr Ile Gln Leu Ile Gln Asn His Phe Val Asp Glu Tyr
                  5                   10                  15
Asp Pro Thr Ile Glu Asp Ser Tyr Lys Arg Gln Val Val Ile Asp Gly
              20                  25                  30
Glu Thr Cys
        35

( 2 ) INFORMATION FOR SEQ ID NO: 14:

( i ) SEQUENCE CHARACTERISTICS:
      ( A ) LENGTH: 15
      ( B ) TYPE: amino acid
      ( C ) STRANDEDNESS:
      ( D ) TOPOLOGY: linear ( x i ) SEQUENCE DESCRIPTION: SEQ ID NO: 14:

Ser Ala Leu Thr Ile Gln Leu Ile Gln Asn His Phe Val Asp Glu
                5                   10                  15

( 2 ) INFORMATION FOR SEQ ID NO: 15:

( i ) SEQUENCE CHARACTERISTICS:

(A) LENGTH: 15
        (B) TYPE: amino acid
        (C) STRANDEDNESS:
        (D) TOPOLOGY: linear (xi) SEQUENCE DESCRIPTION: SEQ ID NO: 15:

Gln Leu Ile Gln Asn His Phe Val Asp Glu Tyr Asp Pro Thr Ile
                5                   10                  15

(2) INFORMATION FOR SEQ ID NO: 16:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 16:

His Phe Val Asp Glu Tyr Asp Pro Thr Ile Glu Asp Ser Tyr Arg
                5                   10                  15

(2) INFORMATION FOR SEQ ID NO: 17:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 17:

Tyr Asp Pro Thr Ile Glu Asp Ser Tyr Arg Lys Gln Val Val Ile
                5                   10                  15

(2) INFORMATION FOR SEQ ID NO: 18:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 18:

Pro Ser Lys Thr Ser Asn Thr Ile Arg Val Phe Leu Pro Asn Lys
                5                   10                  15

(2) INFORMATION FOR SEQ ID NO: 19:

(i) SEQUENCE CHARACTERISTICS:
        (A) LENGTH: 50
        (B) TYPE: amino acid
        (C) STRANDEDNESS:
        (D) TOPOLOGY: linear (xi) SEQUENCE DESCRIPTION: SEQ ID NO: 19:

Met Glu His Ile Gln Gly Ala Trp Lys Thr Ile Ser Asn Gly Phe Gly
                5                   10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
                35                  40                  45

Thr Asp
    50

(2) INFORMATION FOR SEQ ID NO: 20:

(i) SEQUENCE CHARACTERISTICS:
        (A) LENGTH: 15

-continued (B) TYPE: amino acid
(C) STRANDEDNESS:
(D) TOPOLOGY: linear (xi) SEQUENCE DESCRIPTION: SEQ ID NO: 20:

```
Arg Ala Ser Asp Asp Gly Lys Leu Thr Asp Pro Ser Lys Thr Ser
              5                  10                 15
```

INHIBITING PROTEIN INTERACTIONS

This application is a continuation-in-part of application Ser. No. 08/077,256, filed on June 11, 1993 now U.S. Pat. No. 5,582,995.

This invention was made with Government support under DK41513 and DK41762 awarded by the National Institutes of Diabetes and Digestive and Kidney Diseases. The Government has certain rights in the invention.

BACKGROUND OF THE INVENTION

The invention relates to signal transduction.

The ras gene was discovered as an oncogene of the Harvey (rasH) and Kirsten (rasK) rat sarcoma viruses. In humans, characteristic mutations in the cellular ras gene (c-ras) have been associated with many different types of cancers. These mutant alleles, which render Ras constitutively active, have been shown to transform cells, such as the murine cell line NIH 3T3, in culture.

The ras gene product binds to guanine triphosphate (GTP) and guanine diphosphate (GDP) and hydrolyzes GTP to GDP. It is the GTP-bound state of Ras that is active. An accessory molecule, GTPase-activating protein (GAP) also binds to Ras and accelerates the hydrolysis of GTP. The ras proto-oncogene requires a functionally intact raf-1 proto-oncogene in order to transduce growth and differentiation signals initiated by receptor and non-receptor tyrosine kinases in higher eukaryotes. Activated Ras is necessary for the activation of the c-raf-1 proto-oncogene, but the biochemical steps through which Ras activates the Raf-1 protein (Ser/Thr) kinase are not well characterized.

SUMMARY OF THE INVENTION

It has been discovered that zinc-finger domain containing proteins can interact directly with other proteins. Although not being bound by theory, it is believed that the interaction occurs via the zinc-finger domain. (Zinc-finger domains were previously thought to be active primarily in interactions between zinc-finger domain containing proteins and nucleic acids.) For example, a direct interaction between Ras and the regulatory amino-terminal non-catalytic zinc-finger containing domain of Raf has been discovered.

Accordingly, the invention features a method of evaluating a compound, e.g., for the ability to bind to Raf amino-terminal, non-catalytic, zinc-finger domains, for signal-transduction-inhibiting properties, for cell proliferation inhibiting properties, for the ability to alter the cell cycle, or for the ability to inhibit a biological activity, e.g., the ability to bind to another protein, e.g., an oncogene protein or an oncogene protein substrate, of a zinc-finger domain containing protein, an oncogene protein, a cellular oncogene protein, or a proto-oncogene protein. The method includes contacting the compound with a zinc-finger domain containing protein e.g., a signal transduction protein, e.g., an oncogene protein, e.g., Raf, a Ras-binding fragment of Raf, e.g., an amino-terminal, non-catalytic fragment of Raf, e.g., Raf residues 1-257 [Raf(1-257)] [MEHIQGAWKTISNGFGFKDAVFDGSSCISPTIVQQFG YQRRASDDGKLTDPSKTSNTIRVFLP-NKQRTVVNVRNGMSLHDCLMKALKVR-GLQPECCAVFRLLHEHKGKKARLDWNTDAA SLI-GEELQVDFLDHVPLTTHNFARKTFLKLAFCDICQKFL LNGFRCQTCGYKFHEHCSTKVPTMCVD-WSNIRQLLLFNPSTIGDSGVPQLPSLTM-RRMRESVSRMPVSSQHRYSTPHAFT FNTSSPSSEG-SLSQRQRS (SEQ ID NO:1)] or Raf residues 152-168 [Raf(152-168)] [CDICQKFLLNGFRCQTC (SEQ ID NO:2)], a proto-oncogene or a cellular oncogene protein; and determining the ability of the compound to bind to the protein. Preferably, the fragment is a peptide containing residues 1-149 of Raf [MEHIQGAWKTISNGFGFKDAVFDGSSCISPTIVQQFG YQRRASDDGKLTDPSKTSNTIRVFLP-NKQRTVVNVRNGMSLHDCLMKALKVR-GLQPECCAVFRLLHEHKGKKARLDWNTDAA SLI-GEELQVDFLDHVPLTTHNFARKTFLKL (SEQ ID NO:6)] [Raf(1-149)]; more preferably, the fragment is a peptide containing residues 51-131 of Raf [PSKTSNTIRVFLPNKQRTVVNVRNGMSLHDCLMKA LKVRGLQPECCAVFRLLHEHKGKKARLD-WNTDAASLIGEELQVDFL (SEQ ID NO:8)] [Raf(51-131)]; more preferably, the fragment is a peptide containing residues 51-149 of Raf [PSKTSNTIRVFLPNKQRTVVNVRNGMSLHDCLMKA LKVRGLQPECCAVFRLLHEHKGKKARLD-WNTDAASLIGEELQVDFLDHVPLTTHNFARKTFLKL (SEQ ID NO:7)] [Raf(51-149)]; more preferably the fragment is a peptide containing residues 112-143 of Raf [LDWNTDAASLIGEELQVDFLDHVPLTTHNFAR (SEQ ID NO:9)] [Raf(112-143)]; more preferably the fragment is a peptide containing residues 88-105 of Raf [VRGLQPECCAVFRLLHEH (SEQ ID NO:10)] [Raf(88-105)]; most preferably, the fragment is a peptide containing residues 91-105 [LQPECCAVFRLLHEH (SEQ ID NO:11)] [Raf(91-105)]. The binding affinity of the compound for the protein is correlated to one or more of the above mentioned properties. In preferred embodiments, binding can be determined by elution with a second protein known to bind the zinc-finger domain containing protein, e.g., Ras or a Raf-binding fragment of Ras can be used to elute a compound bound to Raf. Other methods can also be used to elute the candidate compound such as the use of antibodies which bind to the protein and thus can disrupt the protein/compound interaction; ionic or non-ionic detergent; chaotropic agents; or altered pH or salt concentration.

In another aspect, the invention features a method of evaluating a compound, e.g., for signal-transduction-inhibiting properties, for cell proliferation inhibiting properties, for the ability to alter the cell cycle, or for the ability to inhibit the biological activity, e.g., the ability to bind to another protein, e.g., an oncogene protein or an oncogene protein substrate, of a zinc-finger domain containing protein, an oncogene protein, cellular oncogene protein or proto-oncogene protein. The method includes contacting the compound with a protein e.g., a signal transduction protein, e.g., an oncogene protein, e.g., Ras, or a Raf-binding fragment of Ras, e.g., Ras residues 1-186 [Ras(1-186)] [MTEYKLVVVGAGGVGKSALTIQLLIQNHFVDEYDP TIEDSYRKQVVIDGETCLLDILDTAGQEEYSAMRDQY MRTGEGFLCVFAINNTKSFEDIHQYREQIKRVKDSDD VPMVLVGNKC DLAARTVESRQAQDLARSYGIPYI-ETSAKTRQGVEDAFYTLVREIRQHKLRKLNPPDESG PQCMSCKC (SEQ ID NO:3)], Ras residues 32-40 [Ras(32-40)] [YDPTIEDSY (SEQ ID NO:4)], or Ras residues 37-51 [EDSYRKQVVIDGETC (SEQ ID NO:12)] [Ras(37-51)], a proto-oncogene or a cellular oncogene protein; and determining the ability of the compound to bind the signal transduction protein. The binding affinity of the compound for the signal transduction protein is correlated to one or more of the above mentioned properties. In preferred embodiments, binding can be determined by elution with a protein known to bind to the signal transduction protein, e.g. Raf, or a Ras-binding fragment of Raf can be used to elute a compound bound to Ras. Other methods can also be used to elute the candidate compound such as the use of antibodies which bind to the signal transduction protein; ionic or non-ionic detergent; chaotropic agents; or altered pH or salt concentration.

The invention also provides a method of evaluating a compound for the ability to inhibit cell proliferation by contacting a candidate compound with Raf or fragment thereof and Ras or a Raf-binding fragment thereof and determining the ability of said compound to interfere with Ras/Raf binding. An increase in phosphorylation of Raf or fragment thereof, e.g., Raf residues 1-50 [MEHIQGAWKTISNGFGFKDAVFDGSSCISPTIVQQFG YQRRASDDGKLTD (SEQ ID NO:19)] [Raf(1-50)], e.g., Raf residues 41-55 [RASDDGKLTDPSKTS (SEQ ID NO:20)] [Raf(41-55)], in the presence of the compound compared to that in the absence of the compound indicates that said compound inhibits cell proliferation. Preferably, Raf phosphorylation is mediated by a signal transduction protein; more preferably, the signal transduction protein is protein kinase A (PKA); and most preferably, Raf is phosphorylated on a serine residue at position 43.

The invention features a method of evaluating a compound for the ability to mimic the ability of the Rap protein to inhibit Raf activation or cell proliferation. The method includes contacting the compound with Raf or a Rap-binding fragment of Raf, e.g., Raf residues 1-257 or Raf residues 152-168, a proto-oncogene protein or a cellular oncogene protein; and determining the ability of the compound to bind to Raf or a fragment thereof. The binding affinity of the compound for Raf or a Rap-binding fragment of Raf is correlated to the above mentioned property. In preferred embodiments, binding can be determined by elution with Rap or a Raf-binding fragment of Rap to elute a compound bound to Raf. Other methods can also be used to elute the candidate compound such as the use of antibodies which bind to Raf; ionic or non-ionic detergent; chaotropic agents; or altered pH or salt concentration.

The screening method described in the previous paragraph can be used to identify candidate compounds with anti-oncogene or tumor suppressor activity. Rap binds to but does not activate wild type Raf, thus it acts as an antagonist of Ras activity. Identification of compounds which bind to Rap-binding sequences of Raf would be likely to mimic the activity of Rap polypeptides, which are identical to Ras in the effector domain (amino acid residues 32-40), have been shown to inhibit the Ras signal transduction pathway and suppress the transformed phenotype in cultured cells.

In another aspect, the invention features a method of evaluating a compound, e.g., for the ability to bind to zinc-finger domains, for signal-transduction-inhibiting properties, for cell proliferation inhibiting properties, for the ability to alter the cell cycle, or for the ability to inhibit the biological activity, e.g., the ability to bind to another protein, e.g., an oncogene protein or an oncogene protein substrate, of a zinc-finger domain containing protein, an oncogene protein, cellular oncogene protein or proto-oncogene protein. The method includes contacting the compound with a zinc-finger domain containing protein and a preselected protein and determining the ability of the compound to interfere with the binding of the preselected protein with the zinc-finger domain containing protein. The ability to interfere with the binding is correlated to the compound's ability to interfere with the zinc-finger domain-containing protein's interaction with the preselected protein and thus to affect one of the properties described above.

In preferred embodiments: the zinc-finger domain containing protein is a first signal transduction protein, e.g., an oncogene protein, e.g., Raf, a proto-oncogene or a cellular oncogene protein; the preselected protein is a protein the biological activity of which is altered, e.g., activated, by the zinc-finger domain containing protein; the preselected protein is a second signal transduction protein, e.g., an oncogene protein, e.g., Ras, a proto-oncogene or a cellular oncogene protein; the preselected protein is a substrate which is phosphorylated or dephosphorylated by the zinc finger-domain containing protein; the first signal transduction protein is Ras or a Raf-binding fragment of Ras, e.g., Ras residues 1-186 or Ras residues 32-40 and the preselected protein is Raf or a Ras-binding fragment of Raf, e.g., Raf residues 1-257 or Raf residues 152-168.

In another aspect, the invention features a method of evaluating the cell proliferation inhibiting properties of a compound. The method includes: contacting the compound with Raf or a Ras-binding fragment of Raf, e.g., Raf residues 1-257 or Raf residues 152-168; contacting the compound with Ras or a Raf-binding fragment of Ras, e.g., Ras residues 1-186 or Ras residues 32-40; and determining the ability of the compound to interfere with the binding of Ras or a Raf-binding fragment of Ras to Raf or a Ras-binding fragment of Raf. The ability to interfere with binding is correlated to the cell proliferation inhibiting properties of the compound.

In another aspect, the invention features a method of screening a candidate compound for the ability to inhibit an interaction of a zinc-finger domain containing protein with a preselected protein. The method includes: (a) providing GAL4 binding site linked to a reporter gene, e.g., the lacZ gene; (b) providing a GAL4 binding domain linked to the zinc-finger domain containing protein or to a biologically active fragment thereof (wherein biologically active means capable of binding to the preselected protein); (c) providing a GAL4 transactivation domain II linked to the preselected protein or a biologically active fragment thereof (wherein biologically active means capable of binding to a zinc-finger containing protein); (d) administering the candidate compound; and (e) monitoring expression of the reporter gene, wherein a decrease in expression is an indication that the candidate compound inhibits an interaction of the zinc-finger domain containing protein and the preselected protein.

In the example above, the zinc-finger domain containing protein is coupled to the GAL4 binding domain and the preselected protein to the GAL4 transactivation domain II. The screening assay of the invention also allows for coupling of the zinc-finger domain containing protein to the GAL4 transactivation domain II and the preselected protein to the GAL4 binding domain.

In preferred embodiments: the zinc-finger domain containing protein is a first signal transduction protein, e.g., an oncogene protein, e.g., Raf, a proto-oncogene protein or a cellular oncogene protein; the preselected protein is a protein the biological activity of which is altered by the zinc-finger domain containing protein; the preselected protein is a second signal transduction protein, e.g., an oncogene protein, e.g., Ras, a proto-oncogene protein or a cellular oncogene protein; the preselected protein is a substrate which is phosphorylated or dephosphorylated by the zinc finger-domain containing protein; the first signal transduction protein is Ras or a Raf-binding fragment of Ras.

In another aspect, the invention features a method of inhibiting unwanted cell proliferation in an animal by administering an effective amount of a compound capable of inhibiting an interaction of Ras with Raf.

In yet another aspect, the invention features, a method of inhibiting unwanted cell proliferation in an animal, e.g., a mammal, e.g., a human. The method includes administering an effective amount of Ras or a Raf-binding fragment of Ras to the animal, wherein the peptide inhibits an interaction of Ras with Raf.

In preferred embodiments, the fragment is a peptide comprising the amino acid sequence of Ras(1-186); the fragment is a peptide comprising the amino acid sequence of Ras(32-40); the fragment is a peptide comprising the amino acid sequence of Ras(37-51).

In another aspect, the invention features, a method of inhibiting unwanted cell proliferation in an animal, e.g., a mammal, e.g., a human. The method includes administering an effective amount of Raf or a Ras-binding fragment of Raf to the animal, wherein the peptide inhibits an interaction of Ras with Raf.

In preferred embodiments, the fragment may be a peptide comprising the amino acid sequence of Raf(1-257), Raf (152-168), Raf(1-149), Raf(51-149), (51-131), Raf(112-143), Raf(88-105), Raf (91-105), or a fragment containing at least 4 consecutive amino acids in the amino acid sequence of Raf(91-105). Preferably, the Raf peptide is not phosphorylated.

The invention also includes a method of inhibiting cell proliferation by administering a phosphorylated Raf or a fragment thereof. The fragment may be a phosphopeptide phosphorylated at the serine at position 43. Preferably the fragment comprises the amino acid sequence of Raf(1-50); more preferably the fragment comprises the amino acid sequence of Raf(41-55).

The invention also includes a peptide capable of inhibiting the interaction of Ras with Raf and containing at least 4 or more amino acids with at least 80% sequence identity to an amino acid sequence of Raf. In preferred embodiments, the amino acid sequence of Raf is the amino acid sequence of Raf((1-149), Raf (51-149), Raf(112-143), Raf(88-105), or Raf(91-105). A peptide having the ability to inhibit the interaction of Ras with Raf and containing 4 to 15 amino acids with at least 95% sequence identity to the amino acid sequence of Raf(91-105) is also within the invention. Preferably, the peptide shares 100% sequence identity with the amino acid sequence of Raf(91-105).

"Identity", as used herein, refers to the subunit sequence similarity between two polymeric molecules, e.g., two peptide molecules. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10, are matched, the two sequences share 90% sequence identity. By way of example, the amino acid sequences VRGLQP and HAFLQP share 50% sequence identity.

In another aspect, the invention includes a peptide capable of inhibiting the interaction of Ras with Raf and containing at least 4 or more amino acids with at least 80% sequence identity to an amino acid sequence of Ras. In preferred embodiments, the amino acid sequence of Ras is the amino acid sequence of Ras(32-40) or Ras(37-51). A peptide having the ability to inhibit the interaction of Ras with Raf and containing 4 to 15 amino acids with at least 95% sequence identity to the amino acid sequence of Ras(37-51) is also within the invention. Preferably, the peptide shares 100% sequence identity with the amino acid sequence of Ras(37-51).

The invention also includes a preparation of antibodies, preferably a monoclonal preparation which consists essentially of antibodies which specifically bind to a peptide consisting of Ras(32-40). In preferred embodiments, the preparation is free of antibodies which bind to epitopes outside the region of Ras residues 32-40. The invention includes a method of inhibiting unwanted cell proliferation in an animal, e.g., a mammal, e.g., a human, by administering a preparation of antibodies of the invention.

An antibody preparation, preferably a monoclonal antibody preparation which specifically binds to a complex comprising Ras bound to Raf, wherein the antibody does not bind to Ras or Raf alone is also within the invention, as well as a method of inhibiting unwanted cell proliferation in an animal, e.g., a mammal, e.g., a human,by administering an antibody, e.g., a monoclonal antibody which binds to the Ras/Raf complex.

In another aspect, the invention features a method of purifying a compound, e.g., an anti-proliferative compound which inhibits the binding of a zinc finger-domain containing protein, e.g., a signal transduction protein, e.g., an oncogene protein, a proto-oncogene protein or a cellular oncogene protein with second protein, e.g., the interaction of Raf or a Ras-binding fragment of Raf with Ras, and isolating said compound by its binding affinity for the zinc finger-domain containing protein. In preferred embodiments, the second protein is a signal transduction protein, e.g., an oncogene protein, e.g., Ras, a proto-oncogene or a cellular oncogene protein; the preselected protein is a substrate which is phosphorylated or dephosphorylated by the zinc finger-domain containing protein; the first signal transduction protein is Ras or a Raf-binding fragment of Ras , e.g., Ras residues 1-186 or Ras residues 32-40 and the preselected protein is Raf or a Ras-binding fragment of Raf, e.g., Raf residues 1-257, Raf residues 152-168, Raf residues 1-149, Raf residues 51-149, Raf residues, 51-131, Raf residues 112-143, Raf residues 88-105, or Raf residues 91-105.

In another aspect, the invention features a method of purifying an anti-proliferative compound. The method includes contacting the compound with Ras or a Raf-binding fragment of Ras, e.g., Ras residues 1-186, Ras residues 32-40 or Ras residues 37-51, and isolating the compound by its binding affinity for Ras or the Raf-binding fragment of Ras.

The invention includes purified preparations of the proteins, peptides, and antibodies of the invention. Purified preparations, used herein, refers to the preparations which are at least 5%, by dry weight the protein, peptide or antibody of the invention.

The term zinc finger domain as used herein refers to a metal coordinating structure formed by two and preferably three cysteine residues spaced apart so as to coordinate a zinc atom, e.g., the structure formed by the amino acid sequence, CXXCXXXXXXXXXXXCXXC (SEQ ID NO:5).

The peptides, proteins and antibodies of the invention can be used to alter receptor and non-receptor mediated signal transduction and inhibit the aberrant proliferation of cells. The screening methods of the invention are simple, rapid and efficient assays designed to identify compounds with anti-proliferative and tumor suppressor activity. Peptides and antibodies of the invention as well as compounds identified using the screening methods of the invention can be used to treat animals, including human patients, afflicted with disease states characterized by disregulated signal transduction or aberrant cell proliferation, such as tumors and autoimmune diseases.

Other features and advantages of the invention will be apparent from the following detailed description and from the claims.

DETAILED DESCRIPTION

The drawings will first be briefly described.

Drawings FIG. 1 is a line graph showing competition between the GTP and GDP bound forms of Ras in the formation of a GST-Raf[1-257]/Ras-GTP-$\gamma$-$^{32}$P complex. Increasing concentrations of Ras-GTP or Ras-GDP were added to a Ras/GST-Raf[1-257] co-precipitation assay and inhibition of complex formation determined. Each curve is representative of three separate experiments.

FIG. 2 is a bar graph showing co-precipitation of Ras-GTP$\gamma$-$^{32}$P by association with truncated versions of c-Raf-1 fused to GST. 10 pmol of GST or GST-[Raf] protein were incubated with Ras-GTP$\gamma$-$^{32}$P followed by precipitation of protein complexes by glutathione-Sepharose and detection by Cerenkov counting. Each bar represents the average of duplicate points from one experiment representative of three separate experiments.

FIG. 3 is a line graph showing competitive inhibition of GAP-stimulated Ras-GTP hydrolysis by GST-Raf competitor proteins. The relative binding affinities for six different deletion mutants of the c-Raf-1 N-terminus were measured by competition for Ras binding with GAP. Increasing concentrations of GST-Raf were included in a standard GAP-Ras-GTPase assay. The binding of Raf proteins to Ras prevented a productive interaction between Ras and GAP. Each curve is representative of three to five different experiments.

FIG. 4A is a diagram of the full length c-Raf-1 protein with major structural features indicated by shaded boxes. CR1 represents the regulatory N-terminus of Raf containing two putative zinc fingers and a site for Ras association. CR2 is also a regulatory region, characterized by heavy phosphorylation on serine and threonine residues. CR3 is the catalytic kinase domain of the protein.

FIG. 4B is a diagram showing the localization of a small domain within the N-terminus of c-Raf-1 which demonstrates high affinity binding to Ras-GTP. Deletions made in the N-terminal domain of Raf are shown along with their relative stability as GST fusions in *E. coli*, ability to co-precipitate Ras and relative binding affinity for Ras-GTP.

FIG. 5 is a bar graph showing protein kinase A (PKA) phosphorylation of truncated GST-Raf proteins. Incorporation of radioactive phosphate into GST and several GST-Raf fusion proteins was measured by nitrocellulose filter binding assay. Specific phosphorylation was only detected when c-Raf-1 serine 43 was intact in the fusion protein. Each bar represents the average of duplicate points from one experiment representative of three separate experiments.

FIG. 6 is a bar graph showing that phosphorylation of c-Raf-1 serine 43 inhibits association between Ras and a truncated N-terminal fragment of c-Raf-1. PKA was incubated with GST, GST-Raf[1-149], GST-Raf[51-149], or GST-Raf[1-149;S43D] in the presence or absence of 0.1 mM ATP for one hour prior to measuring complex formation with Ras-GTP. Counts from GST were subtracted as background. Only the GST-Raf[1-149] protein was inhibited by PKA-dependent phosphorylation. In over five experiments the amount of inhibition observed for GST-Raf[1-149] was 40–60%. No PKA-dependent inhibition was ever observed for the other proteins.

FIG. 11 is a diagram showing the location of five overlapping Ras peptides and inhibition of Ras/Raf association by each peptide.

CONSTRUCTION OF GST FUSION PROTEINS

Figure 1:
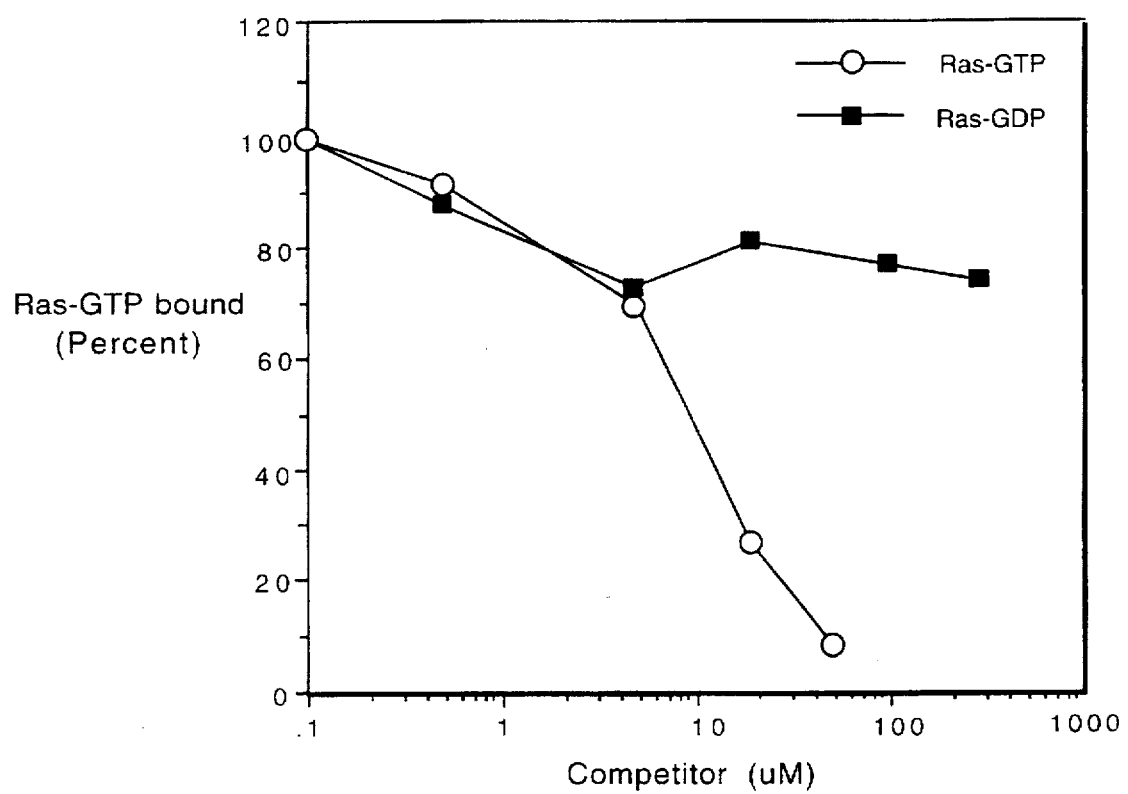

To facilitate the expression, purification, and solid state immobilization of polypeptides such as Ras or Raf, GST fusion proteins can be made. A chimeric gene encoding a GST fusion protein can be constructed by fusing DNA encoding a peptide or peptide fragment to the DNA encoding the carboxyl terminus of GST (see e.g., Smith et al., 1988, Gene 67:31). The fusion construct can be transformed into a suitable expression system, e.g., *E. coli* XA90 in which the expression of the GST fusion protein can be induced with isopropyl-$\beta$-D-thiogalactopyranoside (IPTG).

Purification of GST Fusion Proteins

After transformation of the resulting construct into a suitable expression system, induction with IPTG should yield the fusion protein as a major constituent of soluble, cellular proteins. The fusion proteins can be purified by methods known to those skilled in the art, including purification by glutathione affinity chromatography. The purity of the product can be assayed by methods known to those skilled in the art, e.g., gel electrophoresis.

Binding of Ras to Immobilized GST-Raf

GST fusion proteins can be complexed to glutathione which is attached to a matrix material, e.g., glutathione Sepharose, by methods known to those skilled in the art.

Ras-binding Fragments of Raf; Raf-binding Fragments of Ras

Fragments of Ras which bind Raf (or fragments of Raf which bind Ras) can be made by methods known to those skilled in the art. For example, a DNA fragment which expresses a putative Raf-binding Ras fragment can be fused to GST (as described herein), the fusion protein immobilized by binding to glutathione-Sepharose, and the ability of the fusion protein to bind Raf or a fragment thereof determined.

In vitro Direct Binding of Raf to Ras

Wild type Ras and Rash in which the valine at position 12 has been replaced with glycine (V12GrasH) bind specifically to the aminoterminal regulatory segment of Raf-1 in a GTP dependent fashion. The binding of Ras to Raf(1-257) is strongly dependent on the nature of the guanyl nucleotide bound to Ras. The V12GrasH, charged to a similar extent with either GTP$\gamma$S or GDP$\beta$S, was incubated with the GST-Raf fusion proteins. Significantly less GDP$\beta$S-Ras peptide was retained by Raf(1-257) as compared to incubations containing identical concentrations of Ras peptide in the GTPγS-bound form. Thus the GTP-charged, active form of Ras exhibits a substantially higher apparent affinity for Raf(1-257).

These experiments were performed as follows. The raf-1 gene product has an ATP-binding site, a carboxyterminal catalytic domain and aminoterminal regulatory domains termed CR1 and CR2. Glutathione-S-transferase (GST) fusion proteins were made by cloning DNA sequences encoding an aminoterminal fragment of c-raf-1 comprising the first 257 amino acid residues [Raf(1-257)], and a mutant fragment in which a serine residue replaces a cysteine residue at position 168 [Raf (1-257, $C_{168} \rightarrow S$)]. GST alone was used as a control. Fusion proteins and GST were added at equal concentrations to varying amounts of GTPγS-loaded-V12GrasH. V12GrasH bound to GST-Raf(1-257) in a dose-dependent manner compared to the absence of detectable binding of GTPγS-V12GrasH to GST alone. GTPγS-V12GrasH also binds to the mutant GST-Raf(1-257 $C_{168} \rightarrow S$), however at any concentration of Ras tested, significantly lower amounts of Ras are retained by equal amounts of the mutant Raf(1-257, $C_{168} \rightarrow S$) as compared to the wild-type Raf(1-257).

Incompletely Processed Ras Protein can Bind the Raf Aminoterminal Domain

Ras undergoes a series of sequential posttranslational modifications at its carboxyterminus, consisting of S-farnesylation at $C_{186}$, proteolytic cleavage after $C_{186}$, carboxymethylation of the $C_{186}$ carboxyterminus, and palmitoylation at one or more cysteines upstream (Hancock, J. F. et al. *Cell* 57, 1167–1177 (1989)). When expressed in *Spodoptera frugiperda* (Sf9) cells, approximately 10% of the rash peptide is associated with the membrane fractions, and a substantial portion of this has been shown to be palmitoylated, indicating that the Ras peptide has been fully processed. The cytoplasmic forms of baculoviral rash are not palmitoylated, although some molecules may be farnesylated (Page, M. J. et al. *J. Biol. Chem.* 264, 19147–19156 (1989). The ability of membrane derived and cytoplasmic recombinant V12GrasH polypeptides from Sf9 cells in their ability to bind to GST-Raf(1-257) was compared. The Ras peptides were each purified and charged with $^{35}$S-GTPγS to a stoichiometry of approximately 1.0. At approximately equal concentrations, and under similar conditions, both the cytoplasmic and membrane-derived forms of Ras bound effectively to GST-Raf(1-257) in preference to the mutant GST-Raf(1-257, $C_{168} \rightarrow S$). These data indicate that a fully processed Ras peptide is not essential for the binding of Ras to the Raf aminoterminal domain.

In vitro direct binding experiments were carried out as follows. GST, GST-Raf(1 to 257) and GST-Raf(1-257, $C_{168} \rightarrow S$), immobilized on glutathione-agarose beads, were incubated with GTPγS-loaded, baculoviral recombinant, cytosolic V12GrasH or an equal amount of the same Ras peptide loaded with GDPβS; parallel experiments lacked added Ras. After 6 hours of tumbling at 4° C., the glutathione agarose beads were washed and analyzed for the binding of Ras peptide by sodium dodecyl sulfate-polyacrylamide gel electrophoresis (SDS-PAGE), followed by immunoblotting using a pan-Ras monoclonal antibody-2 (Oncogene Science).

Baculoviral recombinant V12GrasH, partially purified from either the membrane pellet or cytosol, were brought to approximately the same concentration of Ras peptide, loaded in parallel with GTPγS, and incubated with GST-Insulin-receptor-substrate-1 (IRS-1) as a control fusion protein, GST-Raf(1-257), or GST-Raf(1-257, $C_{168} \rightarrow S$) immobilized on glutathione agarose. After 6 hours tumbling at 4° C., the beads were washed and analyzed for the binding of Ras peptide.

Recombinant Ras Peptides

For production of recombinant Ras peptide, Sf9 cells grown in monolayer, were infected at 5 x multiplicity of infection (MOI) with a recombinant baculovirus encoding V12GrasH. Sixty five to 72 hours post infection, cells were harvested as in (Mizuno, T. et al. *Proc. Natl. Acad. Sci. U.S.A.* 88, 6442–6446 (1991)), sonicated, and centrifuged at 100,000 ×g for 1 hour. The Ras peptides in the membrane pellet and cytosol were each purified separately using Mono Q anion exchange chromatography, as in (Mizuno, T. et al. *Proc. Natl. Acad. Sci. U.S.A.* 88, 6442–6446 (1991)) employing 30 mM n-octylglucoside in both purifications. The peak of $^{35}$S-GTPγS binding corresponded to the Ras peptide detected by immunoblotting. Both preparations, (stored at—80 in 20 mM TrisCl, pH8, 5 mM $MgCl_2$, 1 mM EDTA, 1 mM DTT, 30 mM n-octylglucoside, ~0.25 M NaCl) were approximately 10% pure.

Nucleotide loading of Ras was carried out by dilution to the desired peptide concentration, and addition to an equal volume of 2 x loading buffer (0.1 M TrisCl pH 7.5, 15 mM EDTA, 1 mg/ml BSA, 2 mM DTT, 1 mM GTPγS or GDPβS). After 15 min. at 37° C., $MgCl_2$ was added to a final concentration of 12.5 mM, and the Ras peptide was placed on ice. Charging of Ras with $^{35}$S-labeled guanyl nucleotides under these conditions resulted in a stoichiometry near 1.0 for both GTPγS and GDPβS. A mock GTP/GDP charging reaction contained all components except that Ras was replaced by Ras storage buffer. cl Recombinant GST-Raf fusion proteins The DNA sequences encoding Raf-1 amino acid residues 1-257 were generated by the polymerase chain reaction (PCR), using as template the plasmids RSV-C4 and RSV-PM17 (Bruder, J. T., Heidecker, G. & Rapp, U. R. *Genes Dev.* 6, 545–556 (1992)), which encode the wild-type and $C_{168} \rightarrow S$ mutant sequences, respectively. The c-DNA were inserted into pGEX-KG (Guan, K. L. and Dixon J. E., *Anal Biochem.* 192, 262–267 (1991)) at the EcoR1 and Sal1 sites, and sequenced to confirm the mutation and proper in-frame insertion. The GST-Raf fusion proteins, and the GST polypeptide were purified on glutathione agarose, and eluted with glutathione (12.5 mM) in 50 mM TrisCl pH 7.5, 0.15M NaCl, 1 mM DTT, 1.0% Triton-X-100 (Buffer A). Glutathione was removed from the eluted fusion protein by dialysis against buffer A. The GST-Raf(1-257) and GST-Raf (1-257, $C_{168} \rightarrow S$) were indistinguishable on a stained polyacrylamide gel. About 50% of the recombinant peptides were recovered as full-length fusion proteins. The purified GST and GST-Raf fusion proteins were each incubated with glutathione agarose at a concentration of 7 mg peptide/ml settled beads with tumbling at 4° C. for 30 min. The beads were washed 4x and resuspended in buffer A as a 50% suspension. 50 µl of the glutathione agarose suspensions were mixed with 80 µl of GTPγS charged cytosolic Ras, 80 µl of mock GTP charging reaction, or 20 µl of GTP-charged Ras plus 60 µl of mock GTP charging reaction. In parallel, 80 µl of GDPβS charged Ras, 80 µl of mock GDP charging reaction, or 20 µl of GDPβS charged Ras plus 60 µl of mock GDP charging reaction were added to 50 µl of the glutathione agarose bead suspensions. Buffer A (0.6 ml), containing a final concentration of 0.2% BSA, 5 mM $MgCl_2$, 25 mM $ZnCl_2$ pH 7.5, was added to all tubes. The suspension was tumbled at 4° C. for 6 hours, washed 5 x in buffer A, eluted into sodium dodecyl sulfate (SDS), subjected to SDS-PAGE. Following transfer to polyvinylidene difluoride (PVDF) membrane, the membrane was immunoblotted using pan-Ras monoclonal antibody-2 (Oncogene Science) and detected using the enhanced chemiluminescence technique (Amersham).

The membrane-derived and cytosolic Ras preparations were diluted to approximately the same Ras peptide concentration, as assayed by immunoblot and gel staining, charged with GTPγS in parallel, and incubated with immobilized GST fusion proteins as described above. A GST-IRS-1 fusion protein was employed as control in place of GST. The Ras standard peptide was purchased from Oncogene Science.

Raf (1-257) Inhibition of c-rasH GTPase Activity

Raf(1-257) inhibits the Ras-GAP stimulation of c-rasH GTPase. The intrinsic rate of Ras-catalyzed hydrolysis of $\gamma^{32}$P-GTP is not altered by recombinant GST-Raf(1-257). In contrast, the ability of p120 Ras-GAP to stimulate Ras GTPase can be potently inhibited by GST-Raf(1-257) added at a concentration nearly equal to Ras-GAP, whereas GST alone has no effect. The mutant GST-Raf(1-257, $C_{168} \rightarrow S$), at identical concentration, gives significantly less inhibition of Ras-GAP than the wild-type GST-Raf(1-257) peptide.

The ability of recombinant GST, GST-Raf(1-257) and GST-Raf(1-257, $C_{168} \rightarrow S$) to alter c-rasH GTPase activity was determined in the absence and presence of Ras-GAP. The GTPase activity was estimated from the $\gamma^{32}$P-GTP remaining bound to c-rasH after filtration.

In these experiments, baculoviral recombinant c-rasH was expressed and purified from the membrane pellet of Sf9 cells as described for the baculoviral membrane V12GrasH above. The c-rasH was charged with $\gamma^{32}$P-GTP by combining 0.1 ml of c-rasH (approximately 10 μg/ml) in Ras storage buffer with 0.3 ml of 60 mM TrisCl, pH 7.5, 5 mM EDTA, 0.7 mg/ml BSA, 1.5 mM DTT, 4 mM ATP, 0.142 μM $\gamma^{32}$P-GTP (4–6×10$^5$ cpm/pmole) on ice. After 1 hour, 50 μl of 135 mM MgCl$_2$ was added. Loading of c-rasH with $\alpha^{32}$P-GTP was carried out under the same conditions; the $\alpha^{32}$P-GTP-c-rasH was separated from unbound nucleotide by gel filtration (PD-10) in 25 mM TrisCl, pH 7.5, 5 mM MgCl$_2$, 3 mM ATP, 1 mM DTT, and stored on ice. Baculoviral recombinant, full-length human GAP protein was extracted from Sf9 cells by homogenization in 25 mM TrisCl pH 7.5, 1 mM EGTA, 5 mM MgCl$_2$, 1 mM DTT (GAP buffer) and protease inhibitors. The clarified supernatant was subjected to anion exchange chromatography on FastQ Sepharose equilibrated with GAP buffer and eluted with NaCl in a gradient to 0.4M. GAP was detected using a radiolabeled Ras peptide in a filter binding assay. The peak containing Ras-GAP was precipitated at 50% (NH$_4$)$_2$SO$_4$, dialyzed against a modified GAP buffer wherein 25 mM 2-[N-morpholino]ethanesulfonic acid (MES) pH 6.5 replaced Tris, and subjected to MonoS cation exchange chromatography in MES-GAP buffer. Peak fractions were pooled and dialyzed against MES-GAP buffer containing 20% glycerol. 4 μl of GAP (0.03 μg/ml) or MES-GAP buffer were combined with 4 μl of GST, GST-Raf(1-257) or GST-Raf(1-257, $C_{168} \rightarrow S$) (each at 0.1 mg/ml in buffer A). The reaction was started by addition of 20 μl of $\gamma^{32}$P-GTP loaded c-rasH. After 15 min at 30° C., 1 ml of a stop solution containing 25 mM TrisCl pH 8, 0.1M NaCl, 30 mM MgCl$_2$, 2 mM DTT, and 1 mg/ml BSA was added. The mixture was filtered through a BA85 nitrocellulose membrane, washed 3 x with 4 ml of stop solution, and the filters analyzed for retained $^{32}$P-labeled nucleotide. The identity of the $\alpha^{32}$P-labeled nucleotide was analyzed by TLC on polyethyleneimine (PEI) cellulose plates developed in 0.75M KPO$_4$, pH 3.65.

In Situ Binding of Raf to Ras in a Two-hybrid Yeast Expression System

Protein-protein interactions can be identified in vivo using a two-hybrid expression system wherein the activity of a transcriptional activator is reconstituted.

The yeast GAL4 protein consists of functionally distinguishable domains. One domain is responsible for DNA-binding and the other for transcriptional activation. In the two-hybrid expression system, plasmids encoding two hybrid proteins, one containing the GAL4 DNA-binding domain fused to protein a first protein and the other containing the GAL4 activation domain fused to a second protein are introduced into yeast. If the two proteins are able to interact with one another, the ability to activate transcription from promoters containing Gal4-binding sites, upstream activating sequence from GAL1 (UAS$_g$) is reconstituted leading to the expression of a reporter gene.

Protein-protein interactions of multiple Ras variants were detected through the ability of such interactions to reconstitute the transactivating function of the GAL4 protein in a yeast expression system (Durfee, T. et al. *Genes Develop.* 7, 555–569 (1993)). The cDNA sequences encoding c-Raf(1-257) and the c-Raf(1-257, $C_{168} \rightarrow S$) mutant were inserted into the pMA424 plasmid (Chien C. T., Bartel P. L., Sternglanz, R., Fields. S., *Proc. Natl. Acad. Sci. U.S.A.* 88, 9578–9582 (1991)), fused in-frame to DNA sequences encoding GAL4 amino acid residues 1-147 (GAL4 DNA binding domain).

pACT is a vector that encodes DNA sequences corresponding to amino acids 768–881 (GAL4 transactivation domain II) (Kitayama, H., Matsuzaki, T., Ikawa, Y. & & Noda, M. *Cell* 56, 77–84 (1989)). Coexpression of pMA424 Raf(1-257) or pMA424 Raf(1-257, $C_{168} \rightarrow S$) with PACT in a yeast strain that contains a GAL4 binding site (from the upstream activating sequence of Gal1) driving expression of a lacZ reporter gene, did not provide any activation of lacZ expression. Fusion of DNA sequences encoding a V12GrasH peptide in-frame with the GAL4 transactivating domain in pACT led to the appearance of several colonies exhibiting strong lacZ expression in the cotransfection with wild-type Raf(1-257) sequences, but not mutant Raf(1-257, $C_{168} \rightarrow S$).

A decrease in transformation efficiency was observed on expression of the ras sequences, whether transfected with either the wild-type or mutant Raf-1 aminoterminus. Since a fully processed Ras carboxyterminus did not appear critical to the interaction in vitro between Raf(1-257) and Ras described earlier, the V12GrasH DNA sequences in pACT were modified so as to remove the carboxyterminal four amino acid residues (ACT). This truncation completely eliminated the growth inhibitory effect of the pACT encoded ras sequences. Under these conditions, it is evident that the expression of V12GrasHΔCT together with wild-type Raf (1-257) strongly reconstitutes the GAL4-driven expression of lacZ, whereas coexpression of V12GrasH ΔCT with the mutant Raf(1-257, $C_{168} \rightarrow S$) results in very weak expression of lacZ. A similar pattern of lacZ expression was obtained if the Raf(1-257) DNA sequences in pMA424 were exchanged into pACTII, and cotransformed with pMA424 containing the ras or rap 1b inserts.

The Rap 1a (Pizon, V. et al. *Oncogene* 3, 201–204 (1988)) and 1b (Pizon, V., Lerosey, L., Chardin, P. & Tavitian, A.

*Nucleic Acids Res.*16, 7719 (1988)) polypeptides (identical to each other over residues 4–106) are low molecular weight GTP binding proteins identical to Ras in the effector domain (amino acid residues 32–40). Rap-1a (Krev-1) was identified as a suppressor of the transformed phenotype induced by v-rasK in NIH 3T3 cells (Kitayama, H., Matsuzaki, T., Ikawa, Y. & & Noda, M. *Cell* 56, 77–84 (1989)); Rap 1a itself is nontransforming. Rap 1b has been shown to antagonize the action of Ras in *Xenopus oocytes* (Campa, M. J. et al. *Biochem. Biophys. Res. Comm.* 174, 1–5 (1991)). Mutation within the Rap-1 effector domain impairs its ability to act as an inhibitor of Ras transformation (Kitayama, H., Mtsuzaki, T., Ikawa, Y. & Noda, M. *Proc. Natl. Acad. Sci. U.S.A.* 87, 4284–4288 (1990)). These observations suggest that the identical effector domain in Rap-1a /1b and Ras may permit binding to a common Ras effector, and in fact Rap-1a binds Ras-GAP with high affinity (Hata, P. et al. *J. biol. Chem.* 265, 7104–7110 (1990); Frech, M. et al. *Science* 249, 169–171 (1990)); clearly, however, Ras residues 32–40 in the Rap-1a context fails to activate and actually inhibits the Ras signal transduction pathway. In view of these properties, it is noteworthy that V12Grap-1b and the V12Grap-1bΔCT interact strongly with Raf(1-257) to activate lacZ expression, while exhibiting no detectable interaction with the mutant Raf(1-257, $C_{168} \rightarrow S$).

The preferential binding of Ras to the wild-type Raf aminoterminal sequences over mutant Raf confirms the results seen with direct binding experiments in vitro. The ability of wild-type Raf(1-257) and mutant Raf(1-257 $C_{168} \rightarrow S$) to interact with a series of V12GrasHΔCT structures containing mutations in and around the Ras effector domain was evaluated by reconstituting GAL4-dependent lacZ expression in yeast (Table 1).

The Ras effector domain has been identified as a region essential for transformation and Ras binding to p120 Ras-GAP. Mutations in this region have been shown not to alter the biochemical activities intrinsic to Ras, i.e. nucleotide binding and hydrolysis and membrane localization. Two V12GrasHΔCT constructs containing mutations within the effector domain [$D_{38} \rightarrow N$, deletion of P34 (Δ34), $D_{38} \rightarrow A$] known to abrogate Ras binding to GAP as well as Ras transforming activity in NIH 3T3 cells (Table 1) (Marshall, M. S. et al. *Molec. Cell Biol.* 11, 3999–4004 (1991); Marshall, M. S. & Hettich, C.A. *Oncogene* 8, 425–431 (1993)), were examined for interaction with Raf(1-257); both effector mutants failed completely to activate lacZ expression on cotransfection with either the wild-type or mutant raf-1 sequences (Table 1).

Mutation of Ras residues 26, 27, 30, 31 and 45, adjacent to the Ras effector domain, have been shown to impair Ras transforming activity despite modest or no impairment in Ras affinity for Ras-GAP. The effects of mutations at these residues, inserted into the V12GrasHΔCT sequence, on activation of lacZ expression in collaboration with Raf(1-257) is shown in Table 1. The $D_{45} \rightarrow E$ mutation is known to greatly impair Ras transforming activity, despite enhanced binding of this mutant Ras to Ras-GAP and neurofibromatosis-type 1 gene product (NF1), and a normal sensitivity to GAP stimulation of Ras GTPase (Marshall, M. S. & Hettich, C. A. *Oncogene* 8, 425–431 (1993)). The $D_{45} \rightarrow E$ mutation inserted into V12GrasHΔCT construct markedly reduced the ability of V12GrasHΔCT to activate lacZ expression in collaboration with Raf(1-257). The alteration of Ras residues $N_{26}H_{27} \rightarrow G$ and I, respectively, also spares GAP binding and responsiveness while decreasing substantially Ras transforming activity (although somewhat less severely than $D_{45} \rightarrow E$)(Table I) (Marshall, M. S. et al. *Molec. Cell Biol.* 8, 3999–4004 (1991); Marshall, M. S. & Hettich, C. A. *Oncogene* 8, 425–431 (1993)). Insertion of the $G_{26} I_{27}$ mutation into V12GrasHΔCT diminished substantially the activation of lacZ expression on coexpression with Raf(1-257), although to a lesser degree than $D_{45} \rightarrow E$ (Table 1). Alteration of Ras residues $D_{30}E_{31} \rightarrow E$ and K, respectively, reduces Ras binding to GAP and Ras transforming ability in a proportionate manner by 80–90% (Table 1) (Marshall, M. S. et al. *Molec. Cell Biol.* 11, 3999–4004 (1991); Marshall, M. S. & Hettich, C. A. *Oncogene*8, 425–431 (1993)). The $E_{30}K_{31}$ V12GrasHΔCT structure exhibits a modestly impaired ability to stimulate lacZ expression in collaboration with Raf(1-257).

Detection of protein-protein interactions using the two-hybrid system in yeast was carried out as follows. The vector pMA424 (Chien C. T., Bartel P. L., Sternglanz, R., Fields, S., *Proc. Natl. Acad. Sci. U.S.A.* 88, 9578–9582 (1991)) containing either Raf(1-257) or Raf(1-257, $C_{168} \rightarrow S$) DNA sequences fused in frame with the sequences encoding GAL4 (1-147), was cotransformed into yeast together with the pACTII vector containing no insert as a control, or DNA sequences encoding V12GrasH, V12GrasHΔCT, murine rap1b, or rap1bΔCT fused in frame with the GAL4 transactivation domain II. After 3 days growth on selective media, the colonies were replica-plated to selective media, containing 5-bromo-4-chloro-3-indolyl-βD-galactopyranoside (X-gal) and photographed 3 days later.

The DNA sequences encoding Raf(1-257) and Raf(1-257, $C_{168} \rightarrow S$) were prepared by the PCR using the plasmids RSV-C4 and RSV-PM17 (Bruder, J. T., Heidecker, G. & Rapp, U. R. *Genes Dev.* 6, 545–556 (1992)) respectively as templates. The 5' terminus was constructed to insert in frame with the GAL4 (1-147) sequences at the EcoR1 site; the pMA424 Sal1 site was used for the 3' terminus of the raf sequences. The reading frame and the $C_{168} \rightarrow S$ mutation were verified by DNA sequencing. The V12GrasH and the rap1b sequences inserted into pACTII were generated using PCR, and inserted in frame with the GAL4 transactivation domain II sequences using the BamH1 and Xho1 sites. The ACT constructs lacked the DNA sequences encoding the carboxyterminal 4 amino acids of Ras and Rap1b. The rap1b DNA sequences were isolated by PCR using a murine T cell cDNA library. The yeast strain GGY1::171 was transformed with the pMA424 and pACTII vector constructs according to (Ausubel, F. M. et al. in *Current Protocols in Molecular Biology*, Chapter 13, (Wiley Interscience, New York, 1990)) modified by addition of 10% DMSO to the transformation mixture prior to heat shock. Transformants were grown on SDHis⁻Leu⁻ plates as in (Durfee, T. et al. *Genes Develop.* 7, 555–569 (1993); Chien C. T., Bartel P. L., Sternglanz, R., Fields, S., *Proc. Natl. Acad. Sci. U.S.A.* 88, 9578–9582 (1991)) for 3 days before replica plating to X-gal containing plates, which in turn were scored for blue colonies 72 hours later.

Ras effector domain mutants which impair the interaction between V12GrasHΔCT and Raf(1-257) were analyzed as follows. As described above, the variant ras sequences were obtained by the PCR using the cognate sequence encoded in pMV7 (Marshall, M. S. et al. *Molec. Cell Biol.* 11, 3999–4004 (1991); Marshall, M. S. & Hettich, C. A. *Oncogene* 8, 425–431 (1993)) as template. Each pACTII-ras construct was verified by DNA sequencing. The vector pMA424 encoding Raf(1-257) was cotransformed into yeast with the pACTII vector without an insert, containing V12GrasHΔCT, or containing ras constructs containing mutations introduced into the V12GrasHΔCT background: $D_{45} \rightarrow E$, $D38 \rightarrow N$, Δ34, $D38 \rightarrow A$, $N_{26}H_{27} \rightarrow GI$, and

15

$D_{30}E_{31}\rightarrow EK$. After 3 days growth on selective media, the colonies were replica plated to selective media containing X-gal and scored for blue colonies 3 days later. Cotransformations of the same set of pACTII V12GrasHΔCT variants with pMA424 Raf(1-257, $C_{168}\rightarrow S$) were done in parallel. No blue colonies were detected when those transformants were grown on X-gal plates.

In Table 1, the β-galactosidase activity of the selected clones described above is quantified and this activity compared to the known transforming activity and p120 Ras-GAP and NF1 binding of the Ras mutants. Analysis of Ras effector domain mutations on Ras-Raf interaction in yeast and Ras transformation potency in NIH 3T3 cells was carried out as follows. pMA424 encoding Raf(1-257) was cotransformed into yeast with the pACTII encoded V12GrasHΔCT variants. After 3 days growth on selective media, the plates were scraped and an aliquot of each pool was grown in liquid selective media to an $OD_{600}$ of 0.8. A whole cell suspension was permeabilized and assayed in triplicate for β-galactosidase activity using o-nitrophenyl β-D-galactoside (Ausubel, F. M. et al. in *Current Protocols in Molecular Biology*, Chapter 13, (Wiley Interscience, New York, 1990)). The data on transformation efficiencies in NIH 3T3 cells and relative binding to NF1/GAP are taken from (Marshall, M. S. & Hettich, C. A. *Oncogene*8, 425-431 (1993)); the transformation data are for full-length V12GrasH polypeptides, whereas the NF1/GAP binding refers to c-ras peptides.

The data in Table 1 indicate that there is a strong correlation between the ability of these to transfector domain mutants to transform NIH 3T3 cells and their ability to activate lacZ expression by interacting with the Raf aminoterminal regulatory domain.

Ras-Raf Complex

These findings demonstrate that Raf and Ras can bind to each other directly, as measured in vitro using purified peptides and in situ using a yeast expression system dependent on physical reconstitution of GAL4 DNA binding and transactivating domains. The Raf domain that participates in Ras binding is the Raf aminoterminal regulatory region, and the integrity of the Raf cysteine finger, a structure known to be crucial for the interaction of Raf with upstream-activating elements, is likewise crucial for its direct binding with Ras in situ. An intact effector domain of Ras is necessary for interaction with Raf, and mutations in and around the Ras effector domain impair Ras-transforming activity in parallel to the impairment in the ability of Ras to interact with Raf in situ (Table I). The binding of Raf(1-257) to c-rasH does not alter the rate of Ras GTPase, but inhibits the stimulation of Ras GTPase activity by Ras-GAP, consistent with competitive binding of both the Raf and GAP polypeptides to the Ras effector domain. The Ras carboxyterminal domain, including the S-farnesyl moiety, does not appear crucial for Ras-Raf interaction. Rap-1b also interacts strongly with the Raf aminoterminal domain, providing a plausible mechanism for antagonism between Ras and Rap-1a/b, through the generation of a nonproductive Rap-1/Raf complex, as occurs with Rap-1a and Ras-GAP (Quillam, L. A. et al. *Molec. Cell Biol.* 10, 2901-2908 (1990)).

In view of the considerable evidence that identifies Raf as an indispensable downstream effector of the mitogenic response to Ras, the present data show that the Raf-1 kinase is a direct target of the active Ras peptide. The Ras-Raf interaction described herein probably reflects the first step in the Ras-mediated activation of Raf-1 kinase in situ.

16

Screening Assays

The invention can also be used to screen a candidate compound for the ability to inhibit the interaction of Ras with Raf.

In one screening method, the two-hybrid expression system described above can be used to screen for compounds capable of inhibiting Ras-Raf interaction in vivo. In this system, a GAL4 binding site, linked to a reporter gene such as lacZ, is contacted in the presence and absence of a candidate compound with a GAL4 binding domain linked to a Raf fragment and a GAL4 transactivation domain II linked to a Ras fragment. Expression of the reporter gene is monitored and a decrease in said expression is an indication that the candidate compound inhibits the interaction of Ras with Raf.

In another screening method, candidate compounds can be evaluated for anti-proliferative activity by contacting Raf or a Ras-binding fragment of Raf with a candidate compound and determining binding of the candidate compound to the peptide. Raf or Ras-binding fragment of Raf can be immobilized using methods known in the art such as binding a GST-Raf fusion protein to a polymeric bead containing glutathione. Binding of the compound to the Raf peptide is correlated with the ability of the compound to disrupt the signal transduction pathway and thus inhibit cell proliferation.

A co-precipitation competition assay can also be used to measure the relative binding affinities of Ras or fragments and mutants thereof for Raf and fragments and mutants thereof (see Examples 1-5). The effect of various candidate compounds to disrupt or reduce binding can also be measured in such a competition assay.

Candidate compounds can be screened for the ability to bind to Ras or a Raf-binding fragment of Raso Similarly, compounds can be screened as above for the ability to bind to Raf or a Rap-binding fragment of Raf to identify a compound with anti-proliferative activity.

In another screening method, one of the components of the Ras-Raf binding complex, such as Ras or a Raf-binding fragment of Ras or Raf or a Ras-binding fragment of Raf, is immobilized. Peptides can be immobilized using methods known in the art, such as adsorption onto a plastic microtiter plate or specific binding of a GST-fusion protein to a polymeric bead containing glutathione. For example, GST-Raf(1-257) can be bound to glutathione-Sepharose beads. The immobilized peptide is then contacted with the labeled peptide to which it binds (Ras in this case) in the presence and absence of a candidate compound. Unbound peptide can then be removed and the complex solubilized and analyzed to determine the amount of bound labeled peptide. A decrease in binding is an indication that the candidate compound inhibits the interaction of Ras with Raf.

The invention is not limited to screening for compounds which bind to Ras residues 1-186, Ras residues 32-40, Raf residues 1-257 or Raf residues 152-168. One skilled in the art can identify the appropriate Ras or Rap binding fragments of Raf for screening candidate inhibitory or binding compounds by selecting Raf fragments which are capable of binding to Ras or Rap. Similarly, fragments of Ras to be used in screening assays can be identified by their ability to bind to Raf.

A variation of the above-described screening method can be used to screen for another class of candidate compounds which are capable of disrupting a previously-formed Ras-Raf interaction. In this example, a complex comprising Ras or a Raf-binding fragment thereof bound to Raf or a Ras-binding fragment thereof is immobilized as described above and contacted with a candidate compound. The dissolution of the complex by the candidate compound correlates with the ability of the candidate compound to disrupt or inhibit the interaction of Ras with Raf.

Antibodies

Antibodies to Ras-binding peptides of Raf, Raf-binding peptides of Ras, and the Ras-Raf complex are also useful. Specific antibodies which bind to the binding domains of Ras and Raf can be used to inhibit the interaction between the two peptides and their interaction with other ligands. Antibodies which bind to the complex can be also be used therapeutically to inhibit interactions of the complex in the signal transduction pathway leading to cell proliferation. Such antibodies can also be used diagnostically to measure abnormal expression of Ras or Raf, or the aberrant formation of the complex, which may be indicative of a disease state. These antibodies may also be used to study oncogenesis or to study receptor and non-receptor signal transduction pathways.

Peptides of the invention and the Ras-Raf complex can be used as antigens to immunize animals for the production of polyclonal antisera using standard protocols.

Antibodies directed against specific antigens may be detected by any of several methods known to those skilled in the art, e.g., by using an Ouchterlony double diffusion assay or an enzyme-linked immunoabsorbent assay (ELISA). In double diffusion assays, antigen and antibodies are placed in separate wells cut in a matrix, e.g., agarose on the surface of a glass plate. The contents of both wells diffuse through the matrix in all directions. Where the diffusing antigen and antigen-specific antibodies meet, a precipitin line forms. ELISA involves coating a substrate, e.g., well in a plastic dish, with a purified antigen. Serum to be tested is then added to the well. If present, antigen specific antibodies attach to the antigen coating the well. Non-binding material is washed away and a marker enzyme e.g., horse radish peroxidase or alkaline phosphatase, coupled to a second antibody directed against the antigen-specific primary antibody is added in excess and the non-adherent material is washed away. Finally the enzyme substrate is added to the well and the enzyme catalyzed conversion is monitored as indicative of presence of the antigen.

To produce monoclonal antibodies, antibody-producing cells from the challenged animal can be immortalized (e.g. by fusion with an immortalizing fusion partner) to produce monoclonal antibodies. Monoclonal antibody-producing hybridomas can then be screened for antibody binding as described above.

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin.

Peptide Therapy

The methods of the invention are useful in treating diseases characterized by unwanted proliferation of cells. The invention provides methods of inhibiting the Ras-Raf interaction by administering peptides or peptide fragments or analogs thereof.

The term "fragment", as applied to a peptide, will ordinarily be at least about 10 amino acids, usually about 20 contiguous amino acids, preferably at least 40 contiguous amino acids, more preferably at least 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

Analogs can differ from the native peptides of Ras or Raf by amino acid sequence, or by modifications which do not affect the sequence, or by both.

Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the peptide's biological activity. Table 2 lists a number of conservative amino acid substitutions.

Modifications (which do not normally alter primary sequence) include in vivo or in vitro chemical derivitization of peptides, e.g., acetylation or carboxylation. Also included are modifications of glycosylation, e.g., those made by modifying the glycosylation patterns of a peptide during its synthesis and processing or in further processing steps, e.g., by exposing the peptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Modification of these peptides to improve penetration of the blood-brain barrier would also be useful. Peptides may be altered to increase lipophilicity (e.g. by esterification to a bulky lipophilic moiety such as cholesteryl) or to supply a cleavable "targetor" moiety that enhances retention on the brain side of the barrier (Bodor et al., Science 1992, vol. 257, pp. 1698–1700). Alternatively, the peptide may be linked to an antibody specific for the transferrin receptor, in order to exploit that receptor's role in transporting iron across the blood-brain barrier (Friden et al., Science, 1993, vol. 259, pp. 373–377).

Peptides may be administered to the patient intravenously in a pharmaceutically acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

Since blocking the association of Ras with Raf interferes with receptor-mediated activation of immune cells, this method may also be useful in downregulating the immune response in patients with autoimmune diseases such as systemic lupus erythematosus (SLE), type 1 diabetes, and rheumatoid arthritis. Suppression of an immune response using this method may also be useful in the treatment of allograft or xenograft recipients to prevent rejection of a transplanted organ.

Therapeutic administration of a peptide intracellularly can also be accomplished using gene therapy, wherein a nucleic acid which includes a promoter operatively linked to a sequence encoding a heterologous peptide is used to generate high-level expression of the peptide in cells transfected with the nucleic acid. DNA or isolated nucleic acid encoding peptides of the invention may be introduced into cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule in the case of gene therapy.

Raf Protein Domains Involved in Binding to Ras

As described in Examples 1-5 below, the manner in which Ras recognizes and interacts with Raf was characterized. Binding assays and competitive co-precipitation assays were used to measure the relative binding affinities of a variety of Ras mutants for amino-terminal peptides of Raf. The GTP-bound form of Ras as well as the oncogenic forms were found to associate with Raf with up to 35-fold greater affinity that Ras-GDP and effector loop mutants. Unexpectedly, the substitution of Ras activator residues flanking the effector loop, that impair Ras transforming activity and Ras-Raf interaction as measured using the yeast two-hybrid assay, did not alter the ability of Ras to bind to Raf in vitro. Thus, the importance of these effector domain flanking residues for the Ras-Raf interaction in situ may not be attributed to their direct participation in the Ras-Raf binding interaction. These Ras residues may interact with a third element whose contribution might strengthen the affinity of the Ras-Raf complex or lead to activation of the Raf kinase. Deletion analysis of the c-Raf-1 amino terminus defined a stable binding fragment consisting of residues 1-149 which bound to Ras with slightly greater affinity than did the 1-257 fragment containing the zinc finger region. A smaller, but unstable fragment consisting of c-Raf-1 residues 1-131, also bound to Ras, but with reduced affinity. Removal of the first 50 amino acids increased the affinity of the interaction with Ras while deletion of the first 70 residues eliminated complex formation with Ras-GTP. Phosphorylation of the Raf[1-149] fragment on serine 43 by cAMP-dependent protein kinase substantially reduced Ras binding, demonstrating that downregulation of the Ras-Raf pathway by cAMP occurs exclusively through the first 149 amino acids of the c-Raf-1 regulatory domain and does not require full length Raf protein. These data suggest a model of PKA-dependent regulation in which phosphorylation of c-Raf-1 serine 43 induces a protein flap containing residues 1-50 to block the Ras docking site on c-Raf-1.

Compounds that Inhibit the Interaction of Ras with Raf

Investigations of the respective binding surfaces of the Raf and Ras proteins using site-directed mutagenesis and peptide inhibitors has shown that certain peptides, e.g., Raf residues 88-105 and 112-143 as well as Ras residues 32-51, are essential for protein association. Such peptides can be used as models to synthesize therapeutic compounds which inhibit Ras/Raf interaction in vitro and in vivo. Such modeling techniques are known in the art of synthetic chemistry.

For example, small, overlapping sets of amino acid peptides which span the regions of Raf residues 88-105 and 112-143 and Ras residues 32-51 can be synthesized and screened for inhibitory activity. Peptides found to inhibit Ras-Raf interaction can then be used as structural prototypes for the synthesis of conformationally constrained analogs. Peptide bonds within the analogs can be modified or replaced to yield potent, stable, non-peptidyl inhibitors suitable for therapy.

The crystal structure of Ras is known in the art and can thus be used to derive the actual conformation of binding residues 37-51. Similarly, X-ray crystallography of Raf crystals and Ras/Raf co-crystals can be used to predict the inhibitory structure of each peptide spanning Raf residues 91-105, 123-137, and Ras residues 37-51. Modified peptides, e.g., Raf peptides containing a phosphoserine at position 43, e.g., Raf(1-50), e.g., Raf(41-55), which have been found to have inhibitory activity can also be used as models for the synthesis of inhibitory compounds. The structure of the Raf-derived inhibitory peptides can be used to formulate smaller non-peptidyl compounds which mimic essential aspects of the interactive peptide structure. The inhibitory activity of these candidate compounds can then be confirmed using the methods of the invention.

Co-crystals of peptide-Ras and peptide-Raf can be analyzed using X-ray crystallography and nuclear magnetic resonance analysis to determine the structure of the inhibitory peptide in its bound state. Inhibitory peptides can also be characterized by physical chemistry techniques, e.g., circular dichroism, fluorescence, electron spin resonance, that yield data concerning the local environment of the peptides interacting with the protein. Synthetic chemistry techniques can then be used as described above to produce compounds which mimic the inhibitory conformation of each peptide.

EXAMPLE 1

A Quantitative Co-Precipitation Competition Assay for the Determination of the Binding Affinity of Ras for GST-Raf The following reagents used to carry out the methods of the invention are readily available form commercial sources.

Restriction enzymes, vent polymerase and DNA ligase were purchased from New England Biolabs (Beverly, Mass.). GTP-γ-$^{32}$P and ATP-γ-$^{32}$P (specific activity 4500 Ci/mmol) were purchased from ICN Biomedicals. Glutathione-Sepharose, Sephadex G-75 and PD-10 columns were obtained from Pharmacia. NTA-agarose was purchased from Qiagen. Centricon-10 microconcentrators were from Amicon. IPTG was purchased from Bethesda Research Laboratories (Gaithersburg, Md.). All other chemical reagents and the catalytic subunit of the cAMP-dependent protein kinase were purchased from Sigma Chemical Corp. (St. Louis, Mo.).

c-Ha-Ras was expressed in *E. coli* and purified using Mono Q anion-exchange chromatography. In some cases, the Ras protein was further purified by size exclusion chromatography using Sephadex G-75. Ras was bound to radioactively labelled GTP using the following protocol: 132 pmol Ras and 44 pmol GTP-γ-$^{32}$P (specific activity 4500 Ci/mmol) were added to 0.1 ml of 25 mM Tris-HCl, pH 7.5, 2 nM EDTA, 1 mM DTT, and 100 μg/,1 BSA (exchange buffer) and incubated at 30° C. for 20 min. The exchange was halted by placing the reaction on ice. The Ras protein was concentrated in a Centricon-10 microconcentrator, and the free guanine nucleotides removed by washing twice with an excess of ice cold 20 mM Hepes, pH 7.4, and 1 mM MgCl$_2$.

Initially, each fusion protein was made in the *E. coli* strain RR1laci$^q$ grown at 30° C. It was immediately observed that only some of the fusion proteins were made in either soluble or stable form. The GST-Raf(1-257) control was difficult to obtain as a full-length fusion protein, however, addition of a histidine tag to the carboxy-terminus allowed purification of full-length protein using nickel-agarose affinity chromatography. The GST-Raf(1-149) and GST-Raf(51-149) and GST were obtained by expression in *E. coli* strain RR1laci$^q$. These proteins were expressed in soluble form using the DH5α *E. coli* strain grown first at 37° C. to an OD$_{560}$ of 0.5, and then transferred to 20° C. until an OD$_{560}$ of 0.8 was reached. The culture was then induced with 0.5 mM IPTG for one hour to initiate production of the fusion protein. With the exception of GST-Raf(1-257)6XH, all proteins were purified on glutathione-Sepharose beads. Glutathione was removed from the proteins by dialysis against 50 mM Tris-HCl, pH 7.5, 0.15M NaCl, 5% glycerol and 1 mM DTT. Proteins were stored frozen at −80° C. The GST-Raf (1-257) 6XH protein was purified using NTA-agarose affinity chromatography according to the manufacturer's instructions, dialyzed, and stored as described above.

Ras-Raf co-precipitation assays were carried out as follows. Complex formation between GST-Raf(1-257) and Ras-GTP-γ-$^{32}$P was detected by adding 4 μM GST-Raf(1-257) to 12 nM Ras-GTP-γ-$^{32}$P in a 0.03 ml volume of 20 mM Hepes, pH 7.4, 1 mM MgCl$_2$, 1 mg/ml BSA, and 0.3% Triton X-100. After an incubation period of 15 min., 0.2 ml of a 12.5% solution of glutathione-Sepharose beads suspended in 50 mM Tris-HCl pH 7.5, 150 mM NaCl, 1 mM DTT, 1% Triton X-100, 0.2% BSA, and 10 mM MgCl$_2$ (binding buffer) was added, and the mixture tumbled at 4° C. for 30 min. After tumbling, 0.5 ml of binding buffer was added followed by filtering through a glass fiber filter (Millipore GF/F). Filters were washed four times with 1.0 ml of binding buffer, and then the amount of co-precipitated Ras-GTP-γ-$^{32}$P measured by Cerenkov counting. Background counts were determined using GST alone instead of GST-Raf(1-257) and were subtracted from each sample. Relative binding affinities were determined for non-radioactive Ras-GTP and Ras-GDP by adding increasing concentrations of each protein to the co-precipitation assay. The concentration of competitor Ras required to reduce the binding of Ras-GTP-γ-$^{32}$P to GST-Raf(1-257) by 50% provided an IC$_{50}$ value for Raf binding by the competitor protein. The intrinsic rate of Ras-GTP hydrolysis was less than 10% during the course of the Competition assay and had no significant effect on the measured binding constants. The percentage of Ras-GTP-γ-$^{32}$P precipitated was approximately 5–10% with each GST-Raf(1-257) preparation. For comparative co-precipitation of Ras by different GST-Raf mutants, 10 pmol of GST or GST-Raf protein were incubated with Ras-GTP-γ-$^{32}$P, precipitated and quantitated as described above.

Dissociation constants for normal Ras and c-Raf-1 were calculated by competitive inhibition of the Ras-GTP/GAP interaction with the purified N-terminal fragment of the c-RAf-1 protein. This assay was observed to be ineffective for measuring competitive binding between Raf and oncogenic or effector mutant Ras proteins which either lack a functioning GTPase or are deficient in GAP binding. To compare the relative affinity of these types of Ras proteins for the amino-terminus of c-Raf-1, a quantitative Ras-Raf binding assay was developed. Binding of normal Ras protein to a GST-Raf fusion protein was detected by loading Ras with GTP-γ-$^{32}$P prior to incubation with GST-Raf. After mixing the two proteins, GST-Raf/Ras complexes were bound to glutathione-Sepharose to precipitate the GST fusion proteins. The amount of Ras-GTP-γ-$^{32}$P co-precipitated with GST-Raf was measured by quantitating the amount of radioactivity bound to the beads. Relative binding affinities for each mutant Ras protein were obtained by loading the proteins with nonradioactive GTP. The nonradioactively loaded Ras proteins were added at increasing concentrations into the co-precipitation assay as competitors of the Raf/Ras-GTP-γ-$^{32}$P binding interaction. Plotting the inhibition of Ras-GTP-γ-$^{32}$P co-precipitation as a function of competitor concentration gave an IC$_{50}$ value can be used to compare relative binding affinities for Raf.

This method was used to evaluate the interaction between the c-Raf-1 regulatory region (amino acids 1-257) and wild type Ras bound to GTP or GDP (see FIG. 1). Ras-GTP competed in the assay with an IC$_{50}$ value of about 9 μM. Only weak inhibition was detected with Ras-GDP at concentrations up to 300 μM, showing at least a 35-fold difference in binding affinity between the active and inactive forms of Ras. This was consistent with previous qualitative tests of the GTP-dependence of the Ras-Raf interaction. Purified GST protein did not bind to either Ras-GDP or Ras-GTP. The 9 μM IC$_{50}$ value for Ras-GTP was significantly greater than the 150 nM K$_D$ originally observed using a GAP competition assay. In this assay, a greater amount of competitor was required to reach 50% inhibition due to the high concentration of GST-Raf(1-257) used (4 μM). This difference resulted in higher IC$_{50}$ values, but increased the sensitivity and reproducibility of the assay, thus enabling the detection of weakly bound Ras mutants. Experiments using nanomolar amounts of GST-Raf(1-257) reduced the IC$_{50}$ concentration of Ras-GTP to 200 nM, in close agreement with the GAP competition results.

EXAMPLE 2

Measurement of the Relative Binding Affinities of Different Ras Proteins for the c-Raf-1 Regulatory Region Using the co-precipitation competition assay, relative binding constants for the oncogenic Ras[V12]-GTP and Ras[Leu61]-GTP proteins with GST-Raf(1-257) was determined (see Table 3). Both oncogenic forms of Ras bound Raf with affinities similar to normal Ras-GTP. Ras[Leu61] had an $IC_{50}$ of 7 µM, while Ras[V12] bound with slightly greater affinity ($IC_{50}$=4 µM). The relative in vitro binding affinity of the GTP-bound form of seven Ras effector mutants for GST-Raf(1-257) was measured and compared to the known transformation efficiencies of the valine 12 alleles of each mutant in NIH 3T3 cells.

Table 3 shows the relative binding affinities of various Ras proteins for GST-Raf(1-257). The average $IC_{50}$ concentration for competition of Ras-Raf co-precipitation by guanine-nucleotide charged Ras proteins is presented with the standard deviations derived from three to five separate experiments. The values were normalized against Ras-GTP and compared to the known transformation efficiency for each mutant.

The majority of effector mutants were found to be impaired for Raf association with some unexpected exceptions. The non-transforming Ras mutants Ras[Δ34 A 38] and Ras[S35] had $IC_{50}$ values of >200 µM and 180 µM, respectively while the non-transforming Ras[E45] mutant bound with nearly wild type affinity ($IC_{50}$=21 µM). The transformationally impaired Ras[N33], Ras[N38], and Ras[G26I27] mutants had $IC_{50}$ values of 210 µM, >300 µM and 10 µM respectively. The moderately transforming Ras[E20K31] protein bound Raf poorly ($IC_{50}$=226 µM). Since the relative binding affinity for each Ras effector mutant was determined using the glycine 12 form of each protein, rather than valine 12 form as was used in the transformation assays, binding values were measured for the valine 12 form of the Ras [G26I27] and Ras[E45] mutants. No significant difference in $IC_{50}$ values were observed (±5 µM). The addition of 100 mM KCl also had no effect upon the results of these assays. The accuracy of the relative binding affinities observed for GST-Raf by the co-precipitation competition assay was independently confirmed for the Ras-GTP, Ras-GDP, Ras [V12]-GTP, Ras[Δ34 A 38]-GTP, Ras[N38]-GTP and Ras [E45]-GTP proteins using biospecific interaction analysis.

Competition of complex formation between normal, radioactively labeled Ras and a GST-Raf(1-257) fusion protein with non-radioactive Ras proteins established an accurate hierarchy of relative binding affinities for a variety of Ras forms. In vitro binding assays indicated that the GTP-bound form of Ras bound to Raf(1-257) more vigorously than the GDP-bound form, and the co-precipitation competition assay demonstrated that the difference in binding affinity was at least 35-fold. Although it was not possible to make obtain sufficiently high concentrations of Ras-GDP to derive an $IC_{50}$ value for competition, the difference in binding affinity between the GTP and GDP-bound forms was estimated to be approximately 100-fold. This estimation is similar to the differences in apparent dissociation constants observed for Ras-GTP and GDP with the GAP and NF1 proteins.

EXAMPLE 3

Identification of a Minimum c-Raf-1 Fragment Competent for in Vitro Complex Formation with Ras-GTP The Raf(1-149) deletion mutant was constructed by removing the small internal HindIII restriction fragment from the GST-Raf(1-257) expression plasmid, pGEX-KGC4, and religating the truncated c-Raf-1 coding region inframe with a downstream stop codon. Standard recombinant DNA protocols were followed. The GST-Raf(1-131), (51-149) and (71-149) constructs were made using polymerase chain reaction to amplify the corresponding coding region of c-Raf-1, using pGEX-KGC4 as template, followed by subcloning into pGEX-KG vector (Pharmacia). The c-Raf-1 [S43D] mutation was made using the Promega Altered Sites kit. Mutations and clone integrity were confirmed by DNA sequencing with SEQUENASE® (United States Biochemical Corp.)

Using a combination of PCR and restriction fragment drop outs, four subfragments of the GST-Raf(1-257) fusion protein were made which were progressively truncated from Raf amino acid 1 and 257. These deletion mutants encoded c-Raf-1 residues 1-149, 1-131, 51-149 and 71-149 fused to GST. As discussed above, the GST-Raf(1-131) and GST-RAf (71-149) fusion proteins were found to be unstable and difficult to obtain in quantity, suggesting that these deletions may have disrupted a folding domain of the regulatory segment.

Figure 2:
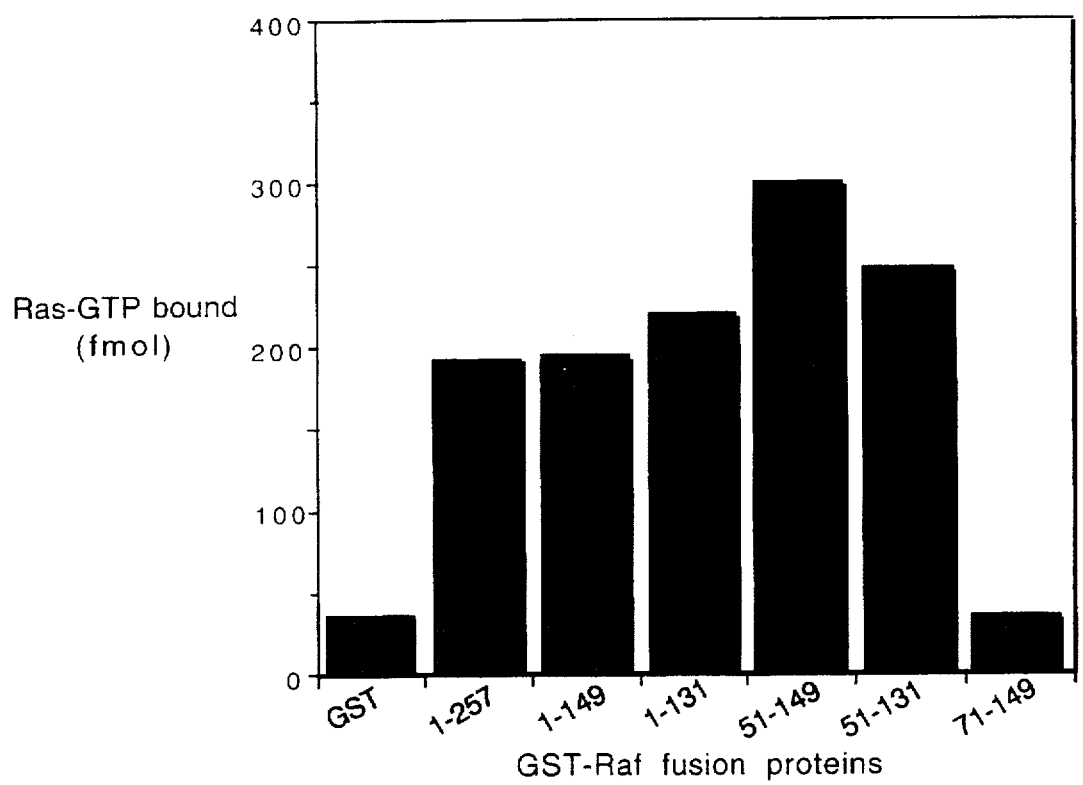

Each GST-Raf fusion protein was analyzed for the ability to form a complex with Ras-GTP-$\gamma$-$^{32}$P by co-precipitation with glutathione-Sepharose (see FIG. 2). The GST-Raf fusion proteins containing residues 1-149, 51-149, and 1-131 lacked the putative zinc finger region, but complexed as well with Ras-GTP as did the zing-finger containing GST-Raf(1-257)6XH protein. Deletion of the first 50 amino acids of c-Raf-1 even increased the amount of Ras co-precipitated. However, removal of the first 70 amino acids completely eliminated stable association with Ras-GTP.

These results were based upon a single concentration of GST-Raf protein, and thus, provided only qualitative data on the interaction between Ras and the truncated Raf proteins. More quantitative measurements were made of the binding affinity of each of the truncated Raf proteins for Ras-GTP by using the GAP competition assay which allows the quantitative measurement of Ras-Raf binding affinity by competitive inhibition of GAP.

GAP competition assays were performed by adding increasing concentrations of GST-Raf proteins or GST to a 0.05 ml reaction volume containing 0.2 nM Ras-GTP-$\gamma$-$^{32}$P, 20 mM Hepes, pH 7.4, 1 mM $MgCl_2$, and 1 mg/ml BSA. The mixture was prewarmed for 2 min. at 30° C. and the reaction was initiated by the addition of GAP(702–1044). The amount of GAP used in each assay equivalent to the quantity able to stimulate the hydrolysis of 50% of the 32P-$\gamma$-GTP bound to Ras under the assay conditions. After a 10 min. incubation at 30° C., the reaction was terminated by the addition of 0.2 ml of cold 5% activated charcoal in 50 mM $NaH_2PO_4$. GTPase stimulation was determined by measuring the amount of free $^{32}$p in the charcoal-free fraction and was expressed as a percentage of activity in the absence of competitor. Counts obtained in the absence of GAP (702–1044) were used as the 0% control value. The concentration of competitor protein required to inhibit GAP stimulated Ras-GTPase activity by 50% ($IC_{50}$) was used as the comparative affinity value.

Figure 3:
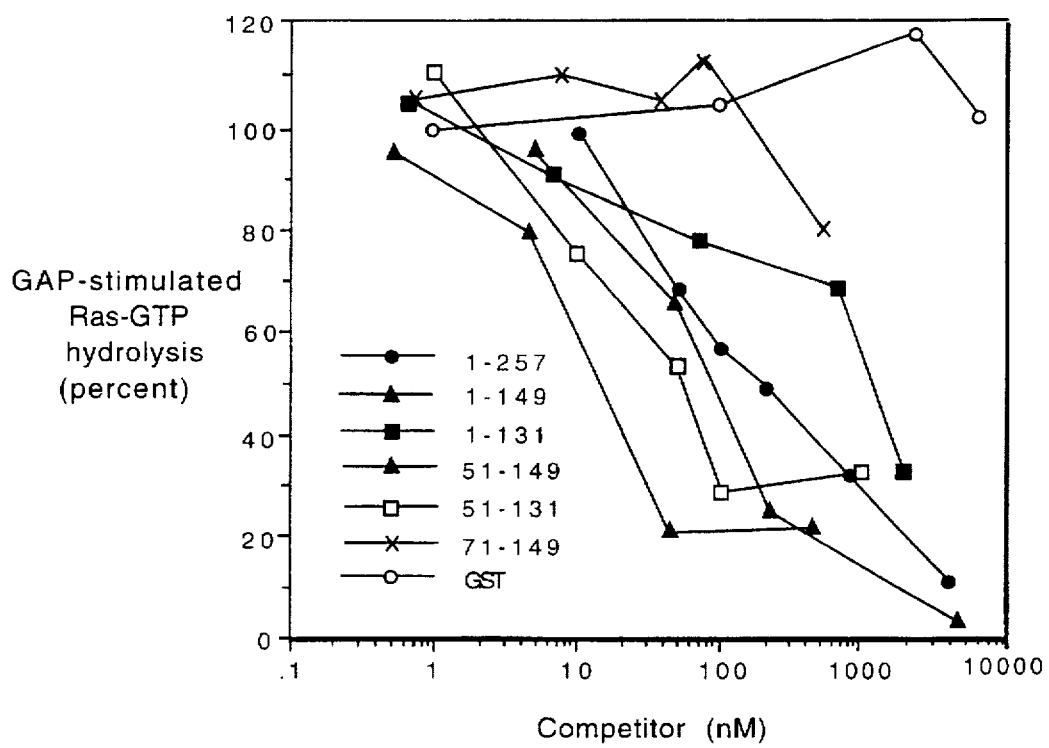
Figure 4:
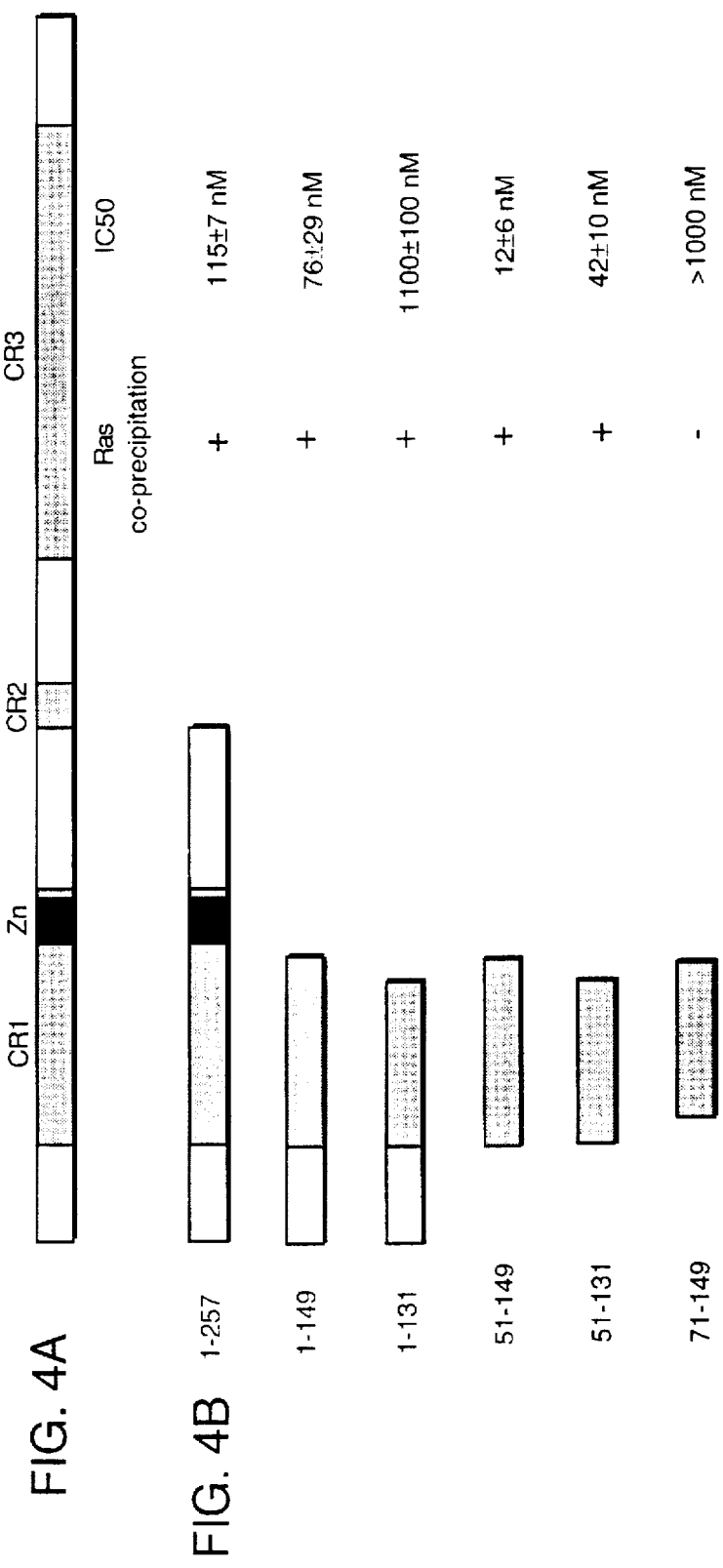
Figure 5:
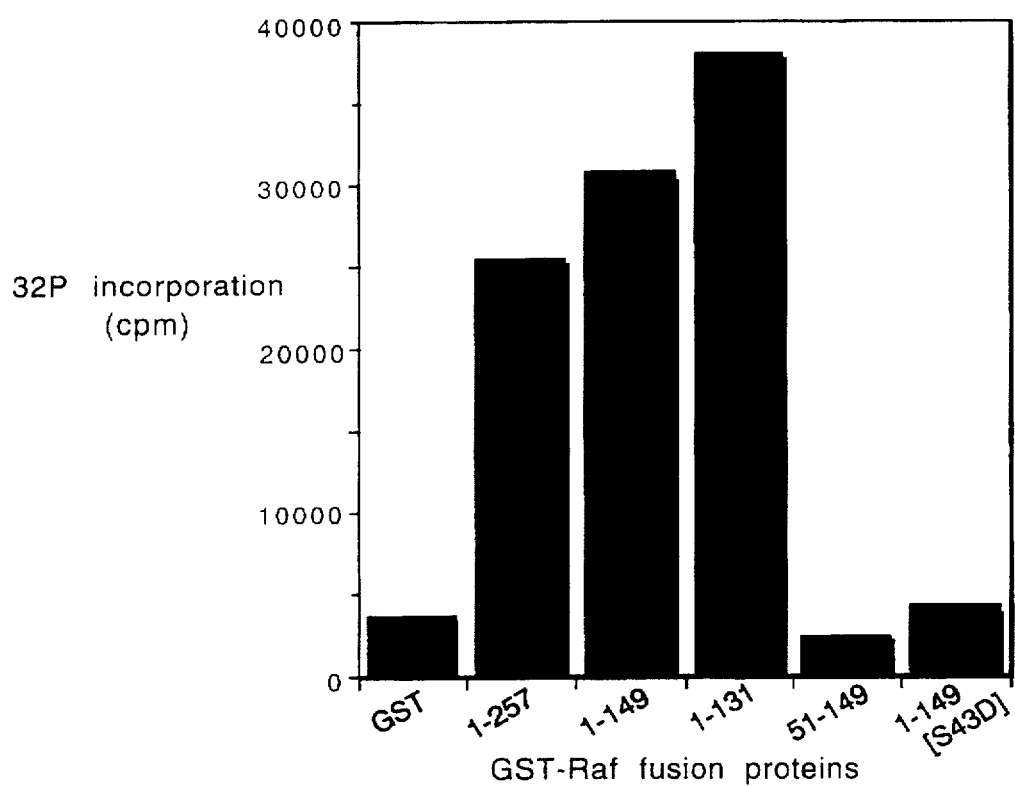

Increasing concentrations of each GST-Raf protein were added to a standard Ras-GTP-$\gamma$-$^{32}$P/GAP reaction, and the concentration of competitor which inhibited GAP stimulation of GTP hydrolysis by 50% was determined. The $IC_{50}$ value reflects the apparent dissociation constant of the complex. Representative competition curves are shown in FIG. 3. Consistent with the co-precipitation data, the GST-Raf(51-149) was found to be the best competitor for Ras binding ($IC_{50}$=12 nM), while the GST-Raf(1-257)6XH and GST-Raf (1-149) proteins competed less well (IC$_{50}$=115 and 76 nM, respectively). Although not reflected in the co-precipitation results, GST-Raf(1-131) protein competed poorly for Ras binding (IC$_{50}$=1,100 nM). Only slight competition was observed with GST-Raf(71-149) at the highest possible concentration, while purified GST did not compete at all. A summary of these results is presented with standard deviations in FIG. 4B.

Oncogenic mutations in Ras have been shown previously to differentially affect binding affinity for GAP and NF1. The Ras[L61] mutant binds to GAP and NF1 50-100-fold better than wild type Ras, while the Ras[V12] mutant had reduced affinity for the GTPase activating proteins. The relative affinities of these two oncogenic Ras proteins were determined for c-Raf-1 and found to be nearly identical to normal Ras. This result suggests that Raf does not interact with the Ras switch 2 region (amino acids 60-76) found to be important for a productive interaction with GAP and NF1. The absence of differences in affinity between normal and oncogenic Ras for Raf suggests that both forms of Ras may activate Raf by an identical mechanism.

Only Ras proteins containing an intact effector loop (residues 32-40) and the flanking activator residues (26,27, 30,31 and 45) can complex efficiently with c-Raf-1 in an intracellular environment. Using purified proteins in vitro, effector mutations at Ras positions 33, 35 and 38 blocked or greatly reduced the binding of Ras and c-Raf-1 proteins. However, mutations at positions 26/27 and 45 flanking the effector loop had no effect on in vitro binding, even though these mutations complexed well with c-Raf-1(1-257) in the two-hybrid system. Although partially interactive in the two-hybrid assay, the transforming Ras[E30K31] mutant was found to be defective for Raf binding when purified components were used. These differences can be explained as follows. Analysis of Ras-Raf interactions in the cell-based yeast two-hybrid assay suggests that the Ras-Raf complexing observed in this system correlates well with mammalian studies examining the ability of various Ras effector mutants to transform cells. If Raf is a physiological effector of Ras, as indicated by extensive genetic and biochemical analysis, it can be concluded that in the yeast cell, protein modifications or solute conditions are appropriate to permit protein-protein interactions to occur as they do in mammalian cells. Such modifications could include phosphorylation by conserved protein kinases like Ste20p, lipid binding or even the ratio of GDP to GTP bound to the Ras proteins. This model is supported by the observation that co-expression of mammalian Ras and c-Raf-1 in S. cerevisiae leads to the activation of c-Raf-1 kinase activity.

Taken together, data from the yeast two-hybrid system and the competition assay suggest that when present in the protein, the integrity of the zinc finger plays a role in in vivo Ras-Raf binding, perhaps mediating proper regulation. It is possible that when both zinc fingers are present on the Raf protein inside a cell, they must remain functional or else the protein structure will be compromised and Ras binding prevented, whereas truncated forms of Raf completely lacking that region would be unaffected by such a switch in conformation.

Analysis of the GST-Raf truncations has enabled the definition of a 99 amino acid domain (residues 51-149) which is both stable and capable of high affinity binding of Ras-GTP. Although c-Raf-1 residues 1-131 are sufficient for binding, the affinity is reduced at least 10-fold relative to residues 1-149. Additionally, the removal of residues 132 to 149 seriously compromises the stability of the fusion protein. Truncation of the N-terminus to generate a fusion protein with c-Raf-1 residues 51-149 actually increases affinity for Ras-GTP by six-fold compared to the GST-Raf (1-149) protein. These data suggest that the N-terminal 50 amino acids possess a negative regulatory function which is relieved by its removal. Deletion of the next 20 amino acids (71-149) results in an unstable protein devoid of Ras binding ability. The high stability and increased affinity for Ras found in the c-Raf-1(51-149) fragment suggests a use for this isolated Ras-binding domain in structure determination and biochemical characterization.

EXAMPLE 4

Phosphorylation of Truncated Raf(1-149) on Serine 43 by cAMP-dependent Protein Dinase A Inhibits Ras Association Purified GST and GST-Raf fusion proteins were tested for the ability to serve as substrates for the catalytic subunit of the cAMP-dependent PKA. Approximately 10 pmol of each protein was incubated with 0.2 unit of purified PKA catalytic subunit in the presence of 0.02 mCi of ATP-γ-$^{32}$P for 30 min at 30° C. in a 0.02 ml reaction volume of 20 mM Tris-HCl, pH 7.5, 1 mM EGTA and 5 mM MgCl$_2$. Incorporation of radioactive phosphate was detected by nitrocellulose filter binding assay and confirmed by SDS-PAGE and autoradiography. Near stoichiometric phosphorylation of the same proteins was obtained with nonradioactive phosphate by incubating 10 pmol of protein with 5 units of PKA catalytic subunit for one hour at 30° C. in a 0.01 ml reaction volume containing 0.1 mM ATP, 20 mM Tris-HCl, pH 7.5, mM EGTA and 5 mM MgCl$_2$. Following the labelling reaction, radioactively-labeled Ras protein was added and co-precipitation of phosphorylated GST-Raf and Ras-GTP measured.

Figure 6:
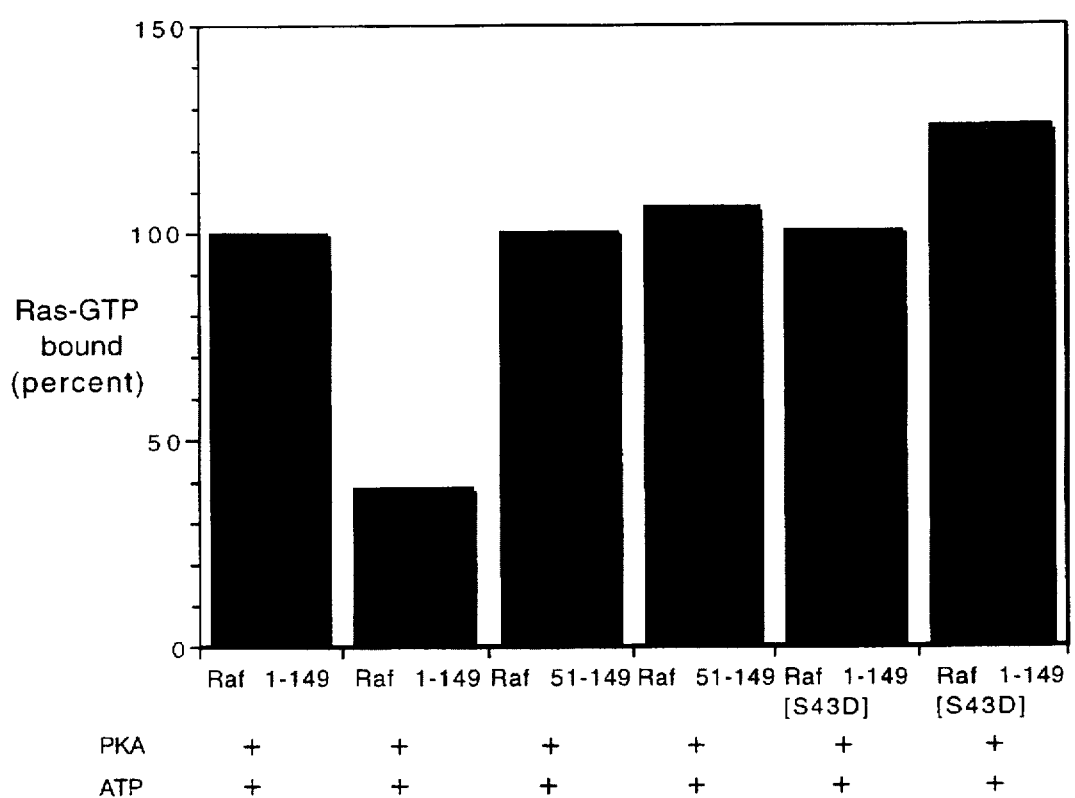

Purified PKA catalytic subunit was incubated with GST, GST-Raf(1-257)6XH, GST-Raf(1-149), GST-Raf(51-149) and GST-Raf[1-149; S43 D] in the presence of ATP-γ-$^{32}$P. Only the Raf fusion proteins containing the first 50 residues of c-Raf-1 were phosphorylated. Mutation of serine 43 to aspartic acid prevented specific phosphorylation by PKA, confirming the identity of this residue as the major phosphoacceptor on the c-Raf-1 N-terminus. Having established that small fragments of c-Raf-1 can be phosphorylated by PKA, inhibition of Ras binding by a phosphorylated N-terminal fragment of c-Raf-1 compared to the full length protein was determined. GST-Raf(1-149), GST-Raf(51-149) and GST-Raf[1-149; S43D] were preincubated with PKA in the presence or absence of ATP and assayed for complex formation with Ras-GTP-γ-$^{32}$P. The GST-Raf(1-149) protein was found to be reproducibly inhibited for Ras binding following phosphorylation by PKA (see FIG. 6). The level of inhibition was consistently greater than 40% from experiment to experiment. Those GST-Raf fusion proteins which lacked the serine at position 43 were unaffected for Ras binding when incubated with PKA and ATP. It was possible that substitution of serine 43 with aspartic acid could mimic a phosphoserine at that position, but the GST-Raf[1-149; S43D] mutant was found to be impaired six-fold for Ras binding. The IC$_{50}$ for competition in the Ras-GAP competition assay was 500 nM compared to 76 nM for the wild type protein.

These data confirmed the identity of c-Raf-1 serine 43 as a regulatory substrate residue for the cAMP-dependent PKA. Phosphorylation of this residue significantly reduces the affinity of c-Raf-1 for Ras-GTP. Such phosphorylation may be one mechanism through which cAMP antagonizes the Ras pathway. The major determinants of phosphate-specific stearic hinderance of Ras binding were found to reside in the small 149 amino acid regulatory domain. Based on the observation that removal of the first 50 amino acids of c-Raf-1 increased affinity for Ras, it is likely that phosphorylation of serine 43 results in a conformational switch which folds a peptide flap over the Ras binding site of c-Raf-1.

In this model, the presence of phosphoserine 43 enhances the affinity of this region for the Ras binding site. The 50 amino acid PKA regulatory segment is only found in c-Raf-1, not A-Raf or B-Raf suggesting that this regulation is unique to the Raf-1 isoform. Since c-Raf-1 is the ubiquitous member of the Raf family, PKA regulation of Ras-Raf binding is likely to be present in most cell types.

EXAMPLE 5

Identification of Sites of Interaction Between c-Raf-1 and Ras-GTP by Contact Epitope Scanning Discrete sites of interaction of Raf with Ras-GTP were located in the regulatory region of c-Raf-1 by contact epitope scanning. For this technique, nineteen peptides were synthesized corresponding to overlapping, fifteen amino acid segments of the 99 residue Ras binding domain of c-Raf-1. Each peptide was tested for its ability to competitively inhibit complex formation between Ras-GTP and GST-Raf(1-257), indicative of peptide binding to Ras. The contribution of each predicted contact epitope was also probed by alanine scanning mutagenesis of the c-Raf-1 regulatory region. The primary site of Ras interaction mapped between residues 88 to 105, with a second, lower affinity site mapping in the region defined by residues 112 to 143. Contact epitope scanning of the Ras effector region found maximum inhibition of Ras-Raf association with a peptide corresponding to amino acids 37-51. The smallest fragment of c-Raf-1 shown to bind Ras with high affinity extends from residue 51 to 149.

Epitope scanning analysis is carried out with a large set of contiguous, overlapping peptides derived from the primary structure of an antigenic peptide. Using the amino acid sequence of this fragment as a template, 19 peptides were synthesized, spanning the c-Raf-1 sequence from residue 41 to 152. All peptides were synthesized by Chiron Mimotopes Peptide Systems using the Multipin peptide synthesis procedure (REF). All peptides were acetylated and ended with a C-terminal amide. Purity was estimated at approximately 70% for the peptide set. Peptides were resuspended in degassed, room temperature dimethylformamide by brief sonication to a concentration of 2 mM.

Each peptide had a length of 15 amino acids and an overlap of approximately ten amino acids with each neighboring peptide. Every peptide was tested for the ability to mimic a Ras binding determinant and behave as a competitor in a standardized Ras-Raf co-precipitation assay. Non-specific effects were ruled out by identical assays using GST or the Ras [N38] effector mutant.

The ability of each peptide to interfere with the co-precipitation of Raf and Ras was measured by adding increasing concentrations of each peptide diluted in 10% DMF to the co-precipitation assay. The concentration of competitor Ras required to reduce the binding of Ras-GTP-$\gamma$-$^{32}$P to GST-Raf(1-257) by 50% provided an IC$_{50}$ value for Raf binding by the competitor peptide. The presence of 10% DMF in the assay had no effect.

Figure 7:
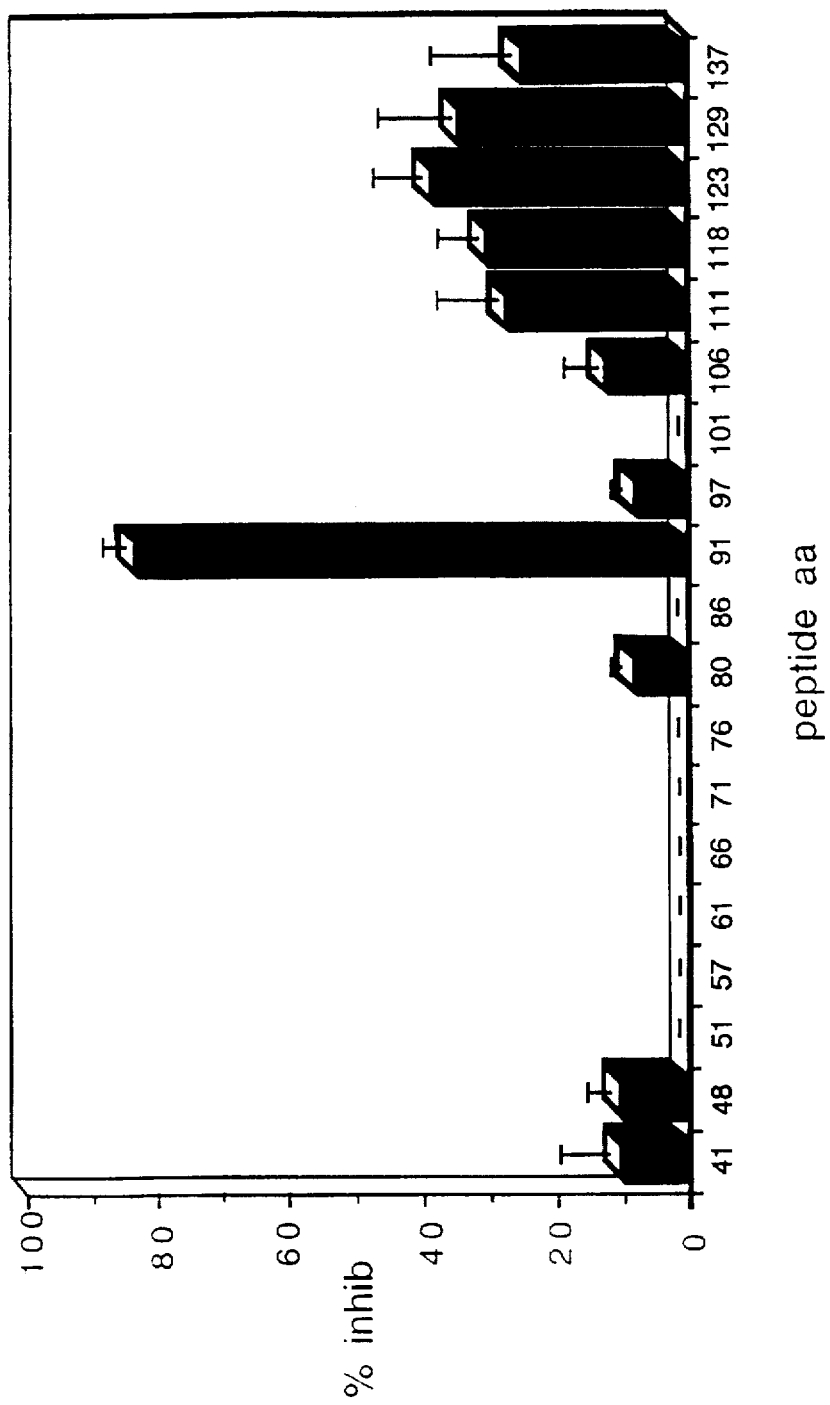
FIG. 7 is a bar graph showing inhibition of Ras/Raf complex formation by synthetic peptides.
Figure 8:
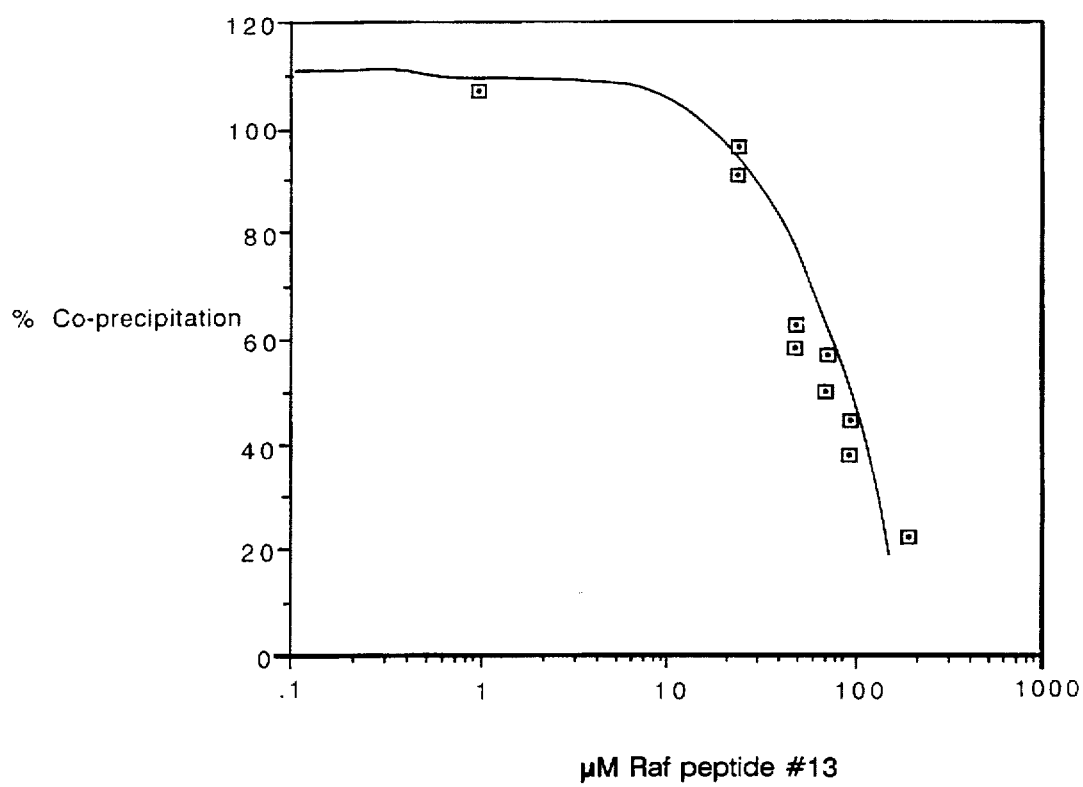
FIG. 8 is a line graph showing inhibition of Ras/Raf complex formation by a synthetic peptide comprising Raf residues 91-105.

Using an initial concentration of 200 mM, six Raf peptides were observed to specifically and reproducibly inhibit Ras-Raf complex formation by 20% or more (FIG. 7) The most competitive peptide contained the c-Raf-1 residues 91-105. Inhibition of Ras-Raf complex formation by this peptide was concentration dependent with an IC$_{50}$ of 73 $\mu$M (FIG. 8). The functional importance of this region of Raf is underscored by the Drosophila D-raf$^{c110}$ mutation that affects late D-raf activity and cell fate in the eye. This mutation corresponds with an arginine to leucine substitution at position 89 in human c-Raf-1, adjacent to the contact epitope defined by the 91-105 peptide. The epitope is probably larger than ten amino acids since little inhibition of Ras-Raf binding was observed for the two overlapping peptides. However, it is possible that the adjacent 86-100 and 96-112 peptides were incapable of assuming a proper conformation in solution. The 80-94 peptide containing arginine 89 was slightly inhibitory.

A separate, but more extended site of Ras interaction was predicted for Raf residues 111-151. The five peptides spanning this region of Raf were all observed to moderately inhibit Ras-Raf association. This result indicates either an extended region of Ras interaction encoded by amino acids 111 to 151, or the presence of smaller clusters of important residues in the overlapping peptides. In support of this observation, the binding affinity of Raf(1-137) was found to be reduced ten-fold compared to Raf(1-149) emphasizing the supportive role of this region for Ras association.

Two other peptides observed to weakly inhibit Ras-Raf association were the 41-55 and 46-60 peptides. This confirms data that demonstrated the regulatory role of this region of the c-Raf-1 N-terminus in preventing Ras binding following the phosphorylation of Raf-1[S43] by protein kinase A (see Example 4). The absence of observable inhibition with other peptides is not conclusive evidence that the regions of Raf that they represent are not contact epitopes. It is possible that they were unable to assume a native conformation in solution within the population of molecules or acquire an induced fit on the surface of Ras. For example, the 66-80 peptide was observed to aggregate upon dilution into the assay, non-specifically precipitating both Ras-GTP and Ras[N38]-GTP, even in the absence of GST-Raf.

As a control, the effects of each peptide on the amount of background precipitation of Ras-GTP with GST protein was determined. None of the competing peptides had any effect on the amount of Ras-GTP available for non-specific interactions, indicating that competition was specific for Ras-Raf complex formation. Another possibility for the observed results is stimulation of Ras GTPase by a peptide. The loss of Ras-GTP would reduce the amount of Ras protein capable of binding to Raf. This possibility was ruled out because no significant increase of GTPase was detected in the presence of any competing peptide.

Data from contact epitope scanning analysis was confirmed by binding studies with an amino-terminal fragment of Raf, Raf(1-149), in which an alanine was substituted for every residue within the 99 amino acid Ras binding domain of c-Raf- 1, with the exception of preexisting alanines, prolines and glycines. Mutations were made in c-Raf-1 using the Promega Altered Sites kit. Mutations and clone integrity were confirmed by DNA sequencing with Sequenase (United States Biochemical Corporation). Mutations were subcloned into the pGEX-KG expression plasmid as EcoRI to HinDIII restriction fragments. The resulting gene fusions provided for the expression of GST-Raf(1-149) fusion proteins that terminated translation at a fortuitous stop codon in the polylinker.

Figure 9:
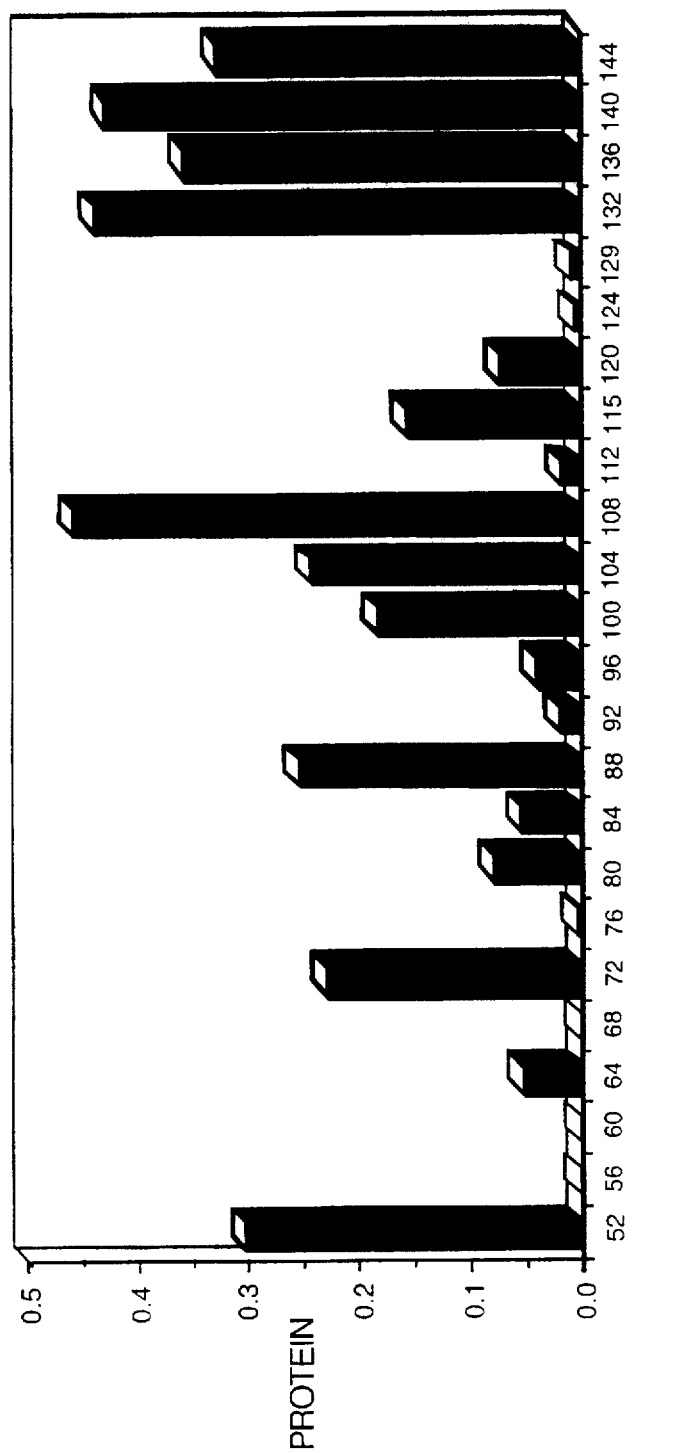
FIG. 9 is a bar graph showing yield of mutant recombinant Raf peptides.

The mutagenesis protocol was simplified by changing three to four adjacent codons to encode alanine in each mutant. The entire region could thus be mutagenically scanned with only twenty-four separate mutants. Each mutant was expressed as a GST-Raf(1-149) fusion protein in *E. coli* and evaluated for protein stability and Ras binding ability. Protein stability was estimated by comparing the yield of soluble mutant GST-Raf protein to wild type GST-Raf. Low yields were indicative of improper folding of the peptide and consequent aggregation or degradation. Percentage protein yields from equivalent culture volumes are shown in FIG. 9. More than half of the mutations resulted in greater than an 80% reduction of soluble protein, suggestive of a loss in structural stability. Many of these mutants had lost highly conserved hydrophobic amino acids, possibly involved in the "packing" of the interior of the domain.

Figure 10:
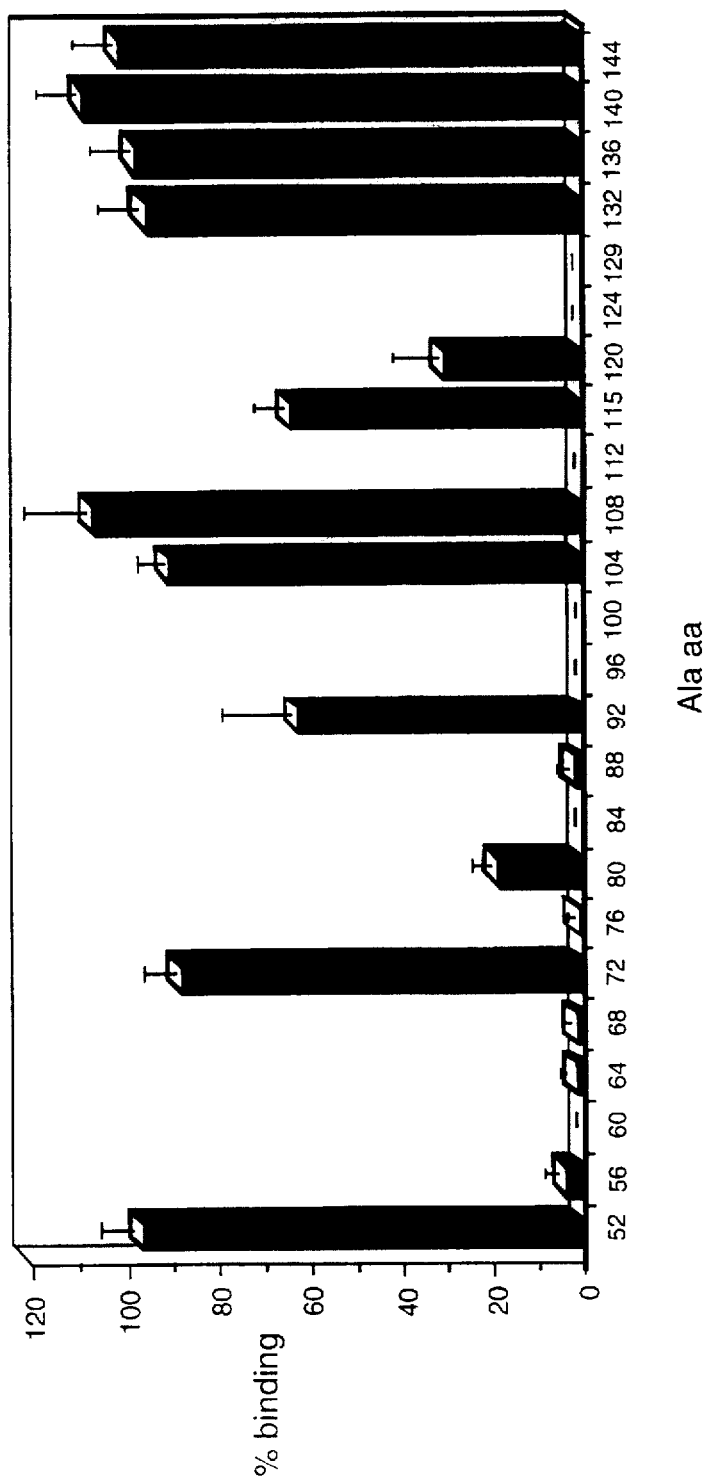
FIG. 10 is a bar graph showing Ras binding to mutant recombinant Raf peptides.

In spite of low yields for some proteins, sufficient quantities of soluble material were obtained to perform Ras co-precipitation assays with each mutant. The Ras binding ability of each mutant Raf protein was then compared to normal GST-Raf(1-149) and is summarized in FIG. 10. Twelve mutants were found to be impaired for Ras association. Out of these twelve, only the 88-91 and 100-103 mutations inhibited Ras binding without significantly affecting protein stability. Surface contact epitopes would be predicted to have minimal contributions to protein folding and thermal stability and maximum contributions to strengthening the association with Ras. This prediction was reenforced by the contact epitope scanning data which implicated Raf residues 91-105 as the high affinity Ras binding site. The 88-91 mutation included a substitution of arginine 89, originally identified in Drosophila as important for Raf function. Mutation of residues 64-67, 84-87 and 96-99 inhibited Ras binding while only moderately destabilizing protein structure, also suggestive of a possible role in Ras-Raf interactions.

The remaining nonbinding mutants were severely compromised structurally, preventing a clear conclusion concerning the involvement of the mutated residues in protein binding. However, reduced protein stability does not necessarily result in a loss in Ras binding. The low yield 92-95 mutant bound quantities of Ras comparable to wild type GST-Raf. Since four peptides overlapping the region of the 124-127 and 128-131 mutations inhibited Ras-Raf association, it is likely that amino acids within the region defined by residues 124-131 are important for both Ras binding and stability. Deletion of residues 132 to 149 from GST-Raf(51-149) reduced binding affinity for Ras only four-fold, suggesting only a minor role in Ras association for C-terminal residues past 131.

In an attempt to localize the site of Raf binding in the Ras protein, five smaller overlapping peptides were synthesized spanning Ras residues 17 to 51 (see FIG. 11). Using the same strategy followed for the Raf peptides, each Ras-derived peptide was measured for competitive inhibition of Ras-Raf binding. While all five peptides reproducibly inhibited complex formation, the C-terminally derived peptides were the best competitors. The Ras 37-51 peptide was most effective with an $IC_{50}$ for inhibition of 100 µM.

When similar peptides were used as competitors of Ras-GAP interactions in a previous study, the opposite gradient of inhibition was observed (Schaber, D. et al., *Proteins: Structure, Function and Genetics* 6:306-315 (1989)). An N-terminally derived Ras peptide (residues 17-32) was a potent competitor of Ras/GAP interaction while more C-terminal peptides (Ras 23-37 or 31-43) did not compete at all. The same results were observed with the Ras peptides shown in FIG. 11 with only the Ras 17-31 peptide capable of competing with Ras for GAP interaction. These results are consistent with genetic analysis of Ras-protein interactions which have suggested that overlapping, yet distinct regions of the Ras protein are involved in GTPase activating protein interaction and effector protein binding and activation. This discrimination suggests that directed inhibitors of Ras-Raf binding can be made which do not interfere with regulation of normal Ras by GAP or neurofibromin.

These data indicate that two primary sites within the Ras binding domain of c-Raf-1 are involved in the interaction with of Raf with Ras-GTP. The primary contact surface is located between residues 88 and 103. This region could contribute to the specificity of Ras-GTP binding with additional stabilizing interactions occurring over the surface defined by residues 111 to 149 centering around residues 124 to 131. It is likely that these regions are interacting directly with the Ras effector region, i.e., residues 26 to 48. The core effector loop would be expected to provide specificity with the surrounding residues, particularly 41 to 51, acting to stabilize the interactione Conservation of essential, complementary charged residues in both Ras (glutamic acid 30, aspartic acid 33, and aspartic acid 38) and c-Raf-1 (lysine 84, lysine 87 and arginine 89) suggest that conserved electrostatic interactions are important for Ras-Raf protein association.

While Ras binding does not directly stimulate the Raf kinase, cooperative interactions with other cellular factors at the plasma membrane ultimately lead to kinase activation. The role of Ras-GTP in the activation of the Raf kinase is primarily as a plasma membrane docking protein. Association with Ras is an indispensable step in the activation of Raf in Ras-transformed cells. The identification and localization of interactive sites using relatively small peptides suggest that blocking peptides and synthetically-derived compounds, e.g., those structurally modeled after blocking peptides, can be used as therapeutic agents to inhibit Ras-Raf association, and hence, Raf activation.

Cell proliferation is the culmination of a successfully transduced intracellular signal. Inhibition of Ras-Raf binding interrupts transduction of an intracellular signal along the Ras signal transduction pathway, and thus, inhibits cell proliferation. The data described herein indicate that inhibition of the Ras-Raf interaction using the compositions and methods of the invention is a promising approach to treating cancer and other diseases characterized by unwanted cell proliferation.

TABLE 1

| pACTII insert | β-Galactosidase (Units ± S.D.) | Transformation efficiency (NIH 3T3 Cells) | Relative NF1/GAP Binding |
|---|---|---|---|
| none | 0.05 ± 0.01 | — | — |
| $V_{12}$ rasH ΔCT | 4.43 ± 0.12 | 1.0 | 1.0 |
| $V_{12}N_{36}$ rasH ΔCT | 0.40 ± 0.01 | 0.01 | 0.28/0.87 |
| $V_{12}D34A_{38}$rasH ΔCT | 0.11 ± 0.01 | <0.001 | <.001/<0.08 |
| $V_{12}E_{45}$rasH ΔCT | nd | <0.001 | 1.3/3.0 |
| $V_{12}G_{26}I_{27}$rasH ΔCT | 1.38 ± 0.03 | 0.04 | 3.91/nd |
| $V_{12}E_{30}K_{31}$rasH ΔCT | 2.83 ± 0.02 | 0.14 | 0.03/0.16 |

TABLE 2

CONSERVATIVE AMINO ACID REPLACEMENTS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Proline | P | D-Pro, L-I-thioazolidine-4-carboxylic acid, D-or L-1-oxazolidine-4-carboxylic acid (Kauer, U.S. Pat. (4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

TABLE 3

| H-Ras mutant | Transformation efficiency† | IC$_{50}$(μM) | Relative Binding Affinity |
|---|---|---|---|
| Ras-GTP | | 9 ± 2 | 1 | 0.10 |
| Ras-GDP | | >300 | >0.03 | — |
| Ras[L61]) | | 7 ± 1 | 1.29 | >1.00 |
| Ras[V12] | | 4 ± 2 | 2.25 | 1.00 |
| Ras[E30K31] | | 226 ± 35 | 0.04 | 0.14 |
| Ras[G26127] | | 10 ± 2 | 0.90 | 0.04 |
| Ras[N38] | | >300 | >0.03 | 0.01 |
| Ras[ 34A38] | | >200 | >0.05 | <0.001 |
| Ras[N33] | | 210 ± 47 | 0.04 | 0.1–0.01 |
| Ras[S35] | | 183 ± 56 | 0.05 | <0.001 |
| Ras [E45] | | 21 ± 3 | 0.43 | <0.001 |

†Transformation efficiency refers to the ability of each protein to form foci relative to Ras[V12] when expressed in NIH3T3 cells. Transformation data is for the valine 12 allele of each mutant with the exception of normal Ras and the leucine 61 mutant.

What is claimed is:

1. A method of evaluating an anti-proliferative compound comprising contacting said compound with an amino-terminal, non-catalytic Ras-binding fragment of Raf and determining the ability of said compound to bind to said fragment, wherein said binding ability of said compound is an indication that said compound inhibits cell proliferation.

2. The method of claim 1, wherein said fragment is a peptide comprising the amino acid sequence of SEQ ID NO:1.

3. The method of claim 2, wherein said fragment is a peptide comprising the amino acid sequence of SEQ ID NO: 6.

4. The method of claim 3, wherein said fragment is a peptide comprising the amino acid sequence of SEQ ID NO: 7.

5. The method of claim 4, wherein said fragment is a peptide comprising the amino acid sequence of SEQ ID NO: 9.

6. The method of claim 5, wherein said fragment is a peptide comprising the amino acid sequence of SEQ ID NO: 10.

7. The method of claim 6, wherein said fragment is a peptide comprising the amino acid sequence of SEQ ID NO: 11.

8. A method of evaluating an anti-proliferative compound comprising contacting said compound with a Raf-binding fragment of Ras comprising an intact effector loop and determining the ability of said compound to bind to said fragment, wherein said binding ability of said compound is an indication that said compound inhibits cell proliferation.

9. The method of claim 8, wherein said fragment is a peptide comprising the amino acid sequence of SEQ ID NO: 3.

10. The method of claim 9, wherein said fragment is a peptide comprising the amino acid sequence of SEQ ID NO: 4.

11. The method of claim 8, wherein said fragment is a peptide comprising the amino acid sequence of SEQ ID NO: 12.

12. A method of evaluating an anti-proliferative compound comprising contacting said compound with Raf or a Rap-binding fragment of Raf and determining the ability to bind to Raf or a fragment thereof.

13. A method of evaluating a compound for the ability to inhibit cell proliferation comprising:
contacting said compound with Raf or a Ras-binding fragment thereof and Ras or a Raf-binding fragment thereof and determining the ability of said compound to interfere with the binding of said Ras or a Raf-binding fragment thereof with said Raf or a Ras-binding fragment thereof, wherein a decrease in said binding in the presence of said compound compared to said binding in the absence of said compound indicates that said compound inhibits cell proliferation.

14. A method of evaluating a compound for the ability to inhibit cell proliferation comprising:
contacting said compound with a Res-binding fragment of Raf and a Raf-binding fragment of Ras and determining the ability of said compound to interfere with the binding of said Raf-binding fragment of Ras with said Ras-binding fragment of Raf, wherein an increase in protein kinase A-mediated phosphorylation of said Raf-binding fragment of Ras in the presence of said compound compared to said phosphorylation in the absence of said compound indicates that said compound inhibits cell proliferation.

15. The method of claim 14, wherein said Raf or a fragment thereof is phosphorylated by a signal transduction protein.

16. The method of claim 15, wherein said signal transduction protein is protein kinase A.

17. The method of claim 16, wherein said Raf or a fragment thereof is phosphorylated on a serine at position 43.

18. A method of evaluating the cell proliferation inhibiting properties of a compound comprising:
contacting said compound with Raf or a Ras-binding fragment of Raf;
contacting said compound with Ras or a Raf-binding fragment of Ras; and
determining the ability of said compound to interfere with the binding of Ras or a Raf-binding fragment of Ras to Raf or a Ras-binding fragment of Raf, said ability to interfere with binding being correlated to the cell proliferation inhibiting properties of said compound.

* * * * *